United States Patent [19]
Schultz et al.

[11] Patent Number: 6,103,722
[45] Date of Patent: *Aug. 15, 2000

[54] ISCHEMIC PRECONDITIONING

[75] Inventors: Jo El Schultz, Green Bay; Garrett Gross, Elm Grove, both of Wis.

[73] Assignee: The Medical College of Wisconsin Research Foundation Inc., Milwaukee, Wis.

[*] Notice: This patent issued on a continued prosecution application filed under 37 CFR 1.53(d), and is subject to the twenty year patent term provisions of 35 U.S.C. 154(a)(2).

[21] Appl. No.: 09/080,665

[22] Filed: May 18, 1998

Related U.S. Application Data

[63] Continuation-in-part of application No. 09/057,632, Apr. 9, 1998, abandoned, which is a continuation-in-part of application No. 08/998,305, Dec. 24, 1997, which is a continuation-in-part of application No. 08/899,370, Jul. 23, 1997, abandoned.

[51] Int. Cl.$^7$ .................................................. A61K 31/495
[52] U.S. Cl. .............................................................. 514/249
[58] Field of Search ............................................. 514/249

[56] References Cited

PUBLICATIONS

Chien et al—J. Mol. Cell. Cardiol 28(9), 1895–1990 (Abstract), 1906.
Schultz et al—Am J. Physiol. 268 (5(AART 4), 1995.
Kobari et al—J. Cereb. Blood FLow Metab., 5(1), 34–9 (Abstract), 1985.
May et al, Adv. Biosoi (Oxford), 25, 531–4 (Abstract), 1985.
Wong et al, J. Mol. Cell. Cardiol. 22(10) 112–75, 1990.
Calderon et al., "Probes for Narcotic Receptor Mediated Phenomena. 19$^1$ Synthesis of (+)–4–[(αR)–α–((2S, 5R)–4–Allyl–2, 5–dimethyl–1–piperazinyl)–3–methoxybenzyl]–N,N–diethylbenzamide (SNC 80): A Highly Selective, Nonpeptide δ Opioid Receptor Agonist", J. Med. Chem., 37:2125–2128 (1994).

Dondio et al., "Discovery of a Novel Class of Substituted Pyrrolooctahydroisoquinolines as Potent and Selective δ Opiod Agonists, Based on an Extension of the Message—Address Concept", J. Med. Chem., 40:3192–3198 (1997).

Negus and Picker, "BW373U86: A Non–Peptidic, Systematically–Active δ Opioid Agonist", CNS Drug Reviews, 2(1):52–74 (1996).

Portughese et al., "A Selective $\delta_1$ Opiod Receptor Agonist Derived from Oxymorphone. Evidence for Separate Recognition Sites for $\delta_1$ Opioid Receptor Agonists and Antagonists", J. Med. Chem., 36:2572–2574 (1993).

Jimenez, I. et al., *Farmacol. Clin. Exp.* (1988) 5(2):265 XP–002079022.

International Search Report for International Application No. PCT/JP98/03288 (1998).

*Primary Examiner*—Raymond Henley, III
*Attorney, Agent, or Firm*—Morrison & Foerster, LLP

[57] ABSTRACT

Methods and pharmaceutical compositions of matter are disclosed and claimed relating to cardioprotective effect mediated by delta (δ) opioid receptor agonists or more specifically delta-1 ($\delta_1$)-opioid receptor agonists. Further, methods drawn to reducing ischemic damage to organs and tissues having delta (δ) opioid receptor agonists or more specifically delta-1 ($\delta_1$)-opioid receptors are disclosed and claimed. Specifically, methods and pharmaceutical compositions of matter are taught as a means of providing cardioprotective treatment through the administration of delta (δ) opioid receptor agonists or more specifically delta-1 ($\delta_1$)-opioid receptor agonists, such as TAN67(-). Said methods and pharmaceutical compositions are envisioned as a means of reducing myocardial infarction arising from the onset and sequelae of myocardial ischemia.

11 Claims, 14 Drawing Sheets

Table 1. Hemodynamic Data obtained in the presence of specific δ-opioid receptor subtype antagonists

|  | n | BASELINE | | | 30 MIN OCC | | | 2 HOURS REP | | |
|---|---|---|---|---|---|---|---|---|---|---|
|  |  | HR | MBP | RPP | HR | MBP | RPP | HR | MBP | RPP |
| Control | 6 | 375±11 | 95±14 | 42±5 | 368±17 | 69±6 | 29±3 | 458±18 | 84±11 | 46±7 |
| Ischemic PC | 6 | 375±9 | 94±10 | 40±3 | 367±15 | 82±14 | 38±4* | 420±22 | 79±14 | 42±6 |
| BNTX | 5 | 350±3 | 81±9 | 36±3 | 388±23 | 86±6 | 42±4* | 406±19* | 70±13 | 39±8 |
| lowBNTX+Ischemic PC | 6 | 360±5 | 103±9 | 45±4 | 392±10 | 94±5* | 46±2* | 457±14 | 83±6 | 51±3 |
| hiBNTX+Ischemic PC | 6 | 352±12 | 85±8 | 38±4 | 402±15 | 84±7 | 44±4* | 440±25 | 70±12 | 43±8 |
| NTB | 5 | 356±16 | 92±3 | 39±2 | 356±12 | 86±4 | 36±2 | 406±18* | 69±4 | 39±2 |
| lowNTB+Ischemic PC | 6 | 370±8 | 94±5 | 41±2 | 372±11 | 68±5 | 33±3 | 440±11 | 64±6 | 38±3 |
| hiNTB+Ischemic PC | 6 | 350±8 | 91±4 | 38±2 | 348±9 | 62±5 | 27±2 | 417±20 | 68±3 | 36±3 |

Abbreviations: HR, heart rate (beats/min). MBP, mean arterial blood pressure (mmHg). RPP, rate-pressure product (mmHg/min/100C). Ischemic PC, 3x five minute ischemic periods. BNTX (3mg/kg, iv), a selective delta1-opioid receptor antagonist, given 10 minutes before the 30 minute occlusion. lowBNTX+Ischemic PC, BNTX (1mg/kg, iv) given 10 minutes before ischemic PC. hiBNTX+Ischemic PC, BNTX (3mg/kg, iv) given 10 minutes before ischemic PC. NTB, naltriben (1mg/kg, iv), a selective delta2-opioid receptor antagonist, given 10 minutes before the 30 minute occlusion. lowNTB+Ischemic PC, naltriben (1mg/kg, iv) given 10 minutes before ischemic PC. hiNTB+Ischemic PC, naltriben (3mg/kg, iv) infused for 60 minutes before ischemic PC.

Values given as mean±SEM; *p<0.05 vs control.

FIGURE 1

Table 2. Hemodynamic Data obtained in the presence of μ- and κ-opioid receptor agonists or antagonists

| | n | BASELINE | | | 30 MIN OCC | | | 2 HOURS REP | | |
|---|---|---|---|---|---|---|---|---|---|---|
| | | HR | MBP | RPP | HR | MBP | RPP | HR | MBP | RPP |
| Control | 6 | 378±13 | 90±7 | 42±3 | 378±15 | 80±7 | 36±3 | 453±21 | 85±7 | 39±5 |
| Ischemic PC | 6 | 343±11* | 90±5 | 36±1 | 372±14 | 80±10 | 38±4 | 407±19 | 70±5 | 39±2 |
| β-FNA+PC | 5 | 364±17 | 75±8 | 35±3 | 376±12 | 51±5* | 25±2* | 428±14 | 58±4* | 34±3 |
| lowDAMGO | 5 | 366±13 | 81±7 | 36±4 | 378±10 | 73±5 | 33±2 | 424±19 | 73±7 | 40±4 |
| medDAMGO | 6 | 392±14 | 89±5 | 42±2 | 382±20 | 52±9* | 25±5* | 440±21 | 54±8* | 32±3 |
| hiDAMGO | 7 | 350±8 | 80±5 | 35±2 | 367±15 | 66±5 | 31±3 | 359±54* | 68±4* | 32±5 |
| lownorBNI+PC | 6 | 372±6 | 78±6 | 35±3 | 387±12 | 66±5 | 34±2 | 445±11 | 53±4* | 33±2 |
| hinorBNI+PC | 6 | 368±10 | 80±5 | 37±2 | 373±8 | 73±4 | 34±1 | 410±12 | 62±7* | 32±3 |

Abbreviations: HR, heart rate (beats/min). MBP, mean arterial blood pressure (mmHg). RPP, rate-pressure product (mmHg/min/1000). Ischemic PC, 3x five minute ischemic periods. β-FNA, β-funaltrexamine (15mg/kg, sc; 24 hour pretreatment), irreversible μ-opioid receptor antagonist, given before ischemic PC. lowDAMGO, 3x 5 minute DAMGO infusions (3x 1μg/kg/infusion), μ-opioid receptor agonist. medDAMGO, 3x 5 minute DAMGO infusions (3x 10μg/kg/infusion), μ-opioid receptor agonist. hiDAMGO, 3x 5 minute DAMGO infusions (3x 100μg/kg/infusion), μ-opioid receptor agonist. lownorBNI, nor-binaltorphine (1mg/kg, iv) given 15 minutes before ischemic PC. hinorBNI, nor-binaltorphine (5mg/kg, iv) given 15 minutes before ischemic PC.

(3x 100μg/kg/5 minute infusion).

Values given as mean±S.E.M., *p<0.05 vs control.

FIGURE 2

Table 3. Infarct Size Data in the presence of BNTX and NTB, specific δ-opioid receptor subtype antagonists

| | n | LV | AAR | IS | IS/AAR |
|---|---|---|---|---|---|
| Control | 6 | 0.847±0.073 | 0.408±0.064 | 0.221±0.039 | 53.2±2.9 |
| Ischemic PC | 6 | 0.777±0.053 | 0.409±0.035 | 0.056±0.019* | 14.1±5.1* |
| BNTX | 5 | 0.791±0.030 | 0.396±0.041 | 0.261±0.048 | 63.8±7.3 |
| lowBNTX+Ischemic PC | 6* | 0.726±0.052 | 0.324±0.061 | 0.063±0.016* | 19.0±3.4* |
| hiBNTX+Ischemic PC | 6 | 0.832±0.058 | 0.433±0.069 | 0.167±0.037 | 38.7±5.4*§ |
| NTB | 5 | 0.776±0.031 | 0.427±0.028 | 0.248±0.022 | 57.9±2.2 |
| lowNTB+Ischemic PC | 6 | 0.777±0.042 | 0.411±0.045 | 0.091±0.027* | 24.4±6.5* |
| hiNTB+Ischemic PC | 6 | 0.710±0.058 | 0.315±0.022 | 0.057±0.009* | 18.1±2.5* |

Abbreviations: n, number of animals. LV, left ventricle in grams. AAR, area at risk in grams. IS, infarct size in grams. IS/AAR, infarct size as a %AAR.

Ischemic PC, 3x five minute ischemic periods. BNTX (3mg/kg, iv), a selective delta1-opioid receptor antagonist, given 10 minutes before the 30 minute occlusion. lowBNTX+Ischemic PC, BNTX (1mg/kg, iv) given 10 minutes before ischemic PC. hiBNTX+Ischemic PC, BNTX (3mg/kg, iv) given 10 minutes before ischemic PC. NTB, naltriben (1mg/kg, iv), a selective delta2-opioid receptor antagonist, given 10 minutes before the 30 minute occlusion. lowNTB+Ischemic PC, naltriben (1mg/kg, iv) given 10 minutes before ischemic PC. hiNTB+Ischemic PC, naltriben (3mg/kg, iv) infused for 60 minutes before ischemic PC.

Values given as mean±S.E.M. There are no significant differences among the groups for the LV and AAR sizes.

IS and IS/AAR in PC, lowBNTX+PC, low- and hiBNTX+PC hearts showed a significant difference compared to control (*$p<0.05$ vs control).

IS/AAR in hiBNTX+PC hearts showed a significant difference compared to control and ischemic PC (§$p<0.05$).

FIGURE 3

Table 4. Infarct Sizes in rat hearts treated with µ- or k-opioid receptor agonists and antagonists

| | n | LV | AAR | IS | IS/AAR |
|---|---|---|---|---|---|
| Control | 6 | 0.842±0.056 | 0.377±0.048 | 0.208±0.034 | 54.7±3.7 |
| Ischemic PC | 6 | 0.755±0.043 | 0.380±0.035 | 0.049±0.017* | 12.0±3.2* |
| β-FNA+PC | 5 | 0.785±0.045 | 0.462±0.045 | 0.040±0.011* | 8.0±1.7* |
| lowDAMGO | 5 | 0.827±0.051 | 0.476±0.051 | 0.265±0.046 | 53.9±4.3 |
| medDAMGO | 6 | 0.831±0.057 | 0.456±0.034 | 0.245±0.034 | 52.9±4.7 |
| hiDAMGO | 7 | 0.807±0.046 | 0.409±0.036 | 0.220±0.047 | 52.0±8.1 |
| lownorBNI+PC | 6 | 0.819±0.040 | 0.430±0.023 | 0.086±0.021* | 20.2±5.1* |
| hinorBNI+PC | 6 | 0.782±0.042 | 0.380±0.040 | 0.076±0.011* | 20.2±2.5* |

Abbreviations: n, number of animals. LV, left ventricle in grams. AAR, area at risk in grams. IS, Infarct size in grams. IS/AAR, Infarct size as a %AAR.

Ischemic PC, 3x five minute ischemic periods. β-FNA, β-funaltrexamine (15mg/kg, sc; 24 hour pretreatment), irreversible µ-opioid receptor antagonist, given before ischemic PC. lowDAMGO, 3x 5 minute DAMGO infusions (3x 1µg/kg/infusion), µ-opioid receptor agonist. medDAMGO, 3x 5 minute DAMGO infusions (3x 10µg/kg/infusion), µ-opioid receptor agonist. hiDAMGO, 3x 5 minute DAMGO infusions (3x 100µg/kg/infusion), µ-opioid receptor agonist. lownorBNI, nor-binaltorphine (1mg/kg, iv) given 15 minutes before ischemic PC. hinorBNI, nor-binaltorphine (5mg/kg, iv) given 15 minutes before ischemic PC.

Values given as mean±S.E.M. There are no significant differences among the groups for the LV and AAR sizes. IS and IS/AAR in PC, β-FNA, low- and hinorBNI treated hearts showed a significant difference (*p<0.05 vs control).

FIGURE 4

ISCHEMIC PRECONDITIONING

This application is a continuation-in-part of prior application Ser. No. 09/057,632 filed on Apr. 9, 1998, now abandoned, which is a continuation-in-part of prior application Ser. No. 08/998,305 filed on Dec. 24, 1997; which is a continuation-in-part of prior application Ser. No. 08/899,370 filed on Jul. 23, 1997, now abandoned. The entire contents of all of these applications are hereby incorporated by reference.

ACKNOWLEDGMENT OF GOVERNMENT SUPPORT

The work described herein was funded in part by a grant from the National Institutes of Health No. HL 08311. The U.S. government has certain rights in this invention.

TECHNICAL FIELD

The present invention relates to methods for inducing a cardioprotective effect via δ-opioid receptor stimulation by administering pharmaceutical compounds. Specifically, the compounds administered include opioid receptor agonists that selectively bind to the delta (δ) opioid receptor.

BACKGROUND ART

Heart disease strikes millions of Americans and represents the leading cause of death. Approximately one million people die each year in the United States from heart and vascular disease (Heart and Stroke Facts, Dallas: American Heart Association, 1993). Impaired coronary blood flow, either partial or total occlusion, results in myocardial ischemia. At least half the number of patients afflicted with myocardial ischemia suffer from further coronary pathology where heart tissue dies from anoxia or lack of oxygen. This pathology, myocardial infarction, can further result in other manifestations of coronary disease including cardiac arrhythmias (Downey and Mullane, Methods for protecting tissues and organs from ischemic damage U.S. Pat. No. 5,573,772; which is hereby incorporated by reference in its entirety herein).

Damage to myocardial tissue from ischemia, decreased oxygenated blood flow to muscle tissue, can be reduced by preconditioning. Brief periods (5–10 minutes) of ischemia have been shown to precondition against more prolonged periods of ischemia. Such preconditioning appears to provide protection against greater pathologic effects on myocardial tissue that arise from ischemia compared with tissues not preconditioned. Additional pathology results from reperfusion injury which occurs following a return of blood flow to previously ischemic myocardium. Preconditioning therefore, may serve as a form of preventive therapy to those patients presenting with impaired coronary vascular disease.

Opioid receptor activation has been implicated to elicit a protective effect during situations of stress produced by hypoxia, ischemia, cold or acidic environments (for example, see: Arrigo-Reina R, Ferri S. Evidence for an involvement of the opioid peptidergic system in the reaction to stressful condition. *Eur J Pharmacol* 1980:64:85–88; and Mayfield, K. P., D'Alecy L. G. Role of endogenous opioid peptides in the acute adaptation to hypoxia. *Brain Res.* 1992;582:226–231) The delta (δ) opioid receptor has been demonstrated to play a major role in this protection. Chien, S. et al., *J Thorac Cardiovasc Surg* (1994) 107:964–967; and Mayfield, K. P., et al., *J Pharmacol Exp Ther* (1994) 268:683–688 and *J Pharmacol Exp Ther* (1994) 268:74–77; and Schultz, J. J. et al., *J Mol Cell Cardiol* (1997) (in press) showed using DPDPE (selective delta-1 ($\delta_1$) opioid receptor agonist) and BNTX (selective delta-1 ($\delta_1$) opioid receptor antagonist) that the delta-1 ($\delta_1$) opioid receptor mediated the adaptation or increased survival time of mice to hypoxic environments. Furthermore, Chien, S. et al., demonstrated that the time prior to organ transplantation was increased significantly from a 6 hour window to a 48 hour window following the administration of a synthetic delta (δ) opioid receptor agonist, DADLE. These delta (δ) opioid receptors have been shown to be involved in the cardioprotective effect of ischemic PC in the intact rat heart. Schultz, J. J., et al., *J Mol Cell Cardiol* (1997) (in press).

Specifically, recent studies have demonstrated that opioid receptors are involved in ischemic preconditioning (PC) in an intact rat model (Schultz, J. J. et al., *Am J Physiol* (1995) 268:H2157–H2161 and Schultz, J. J. et al., *Circ Res* (1996) 78:1100–1104). Additional studies showed that naloxone, a non-selective opioid receptor antagonist, blocked the cardioprotection afforded by brief periods of ischemia (Schultz, J. J. et al., *Am J Physiol* (1995) 268:H2157–H2161). Furthermore, a non-selective opioid receptor agonist, morphine, has been found to mimic the cardioprotective effect of ischemic PC and that this morphine-induced myocardial protection was antagonized by naloxone (Schultz, J. J. et al., *Circ Res* (1996) 78:1100–1104). Subsequent research has provided evidence that opioid receptors are involved in ischemic PC in the rabbit heart, Chien, GL. and Van Winkle, D. M., *J Mol Cell Cardiol* (1996) 28:1895–1990. Other recent studies demonstrated that morphine was cardioprotective in the isolated rabbit heart, Miki, T. and Downey, J., *J Mol Cell Cardiol* (1996) 28:A187.

Myocardial binding studies have shown that δ and κ-opioid receptors are present on ventricular myocytes of the rat (Krumins, S. A., et al., *Biochem Biophys Res Comm* (1985) 127:120–128; Ventura, C., et al., *Biochem Biophys Acta* (1989) 987:69–74; Tai, K. K., et al., *J Mol Cell Cardiol* (1991) 23:1297–1302; Zhang, W-M., et al., (1996) *J Mol Cell Cardiol* 28: 1547–1554; Zimlichman, R., et al., (1996) *Circulation* 93: 1020–1025). Also, δ- and κ-opioid receptors have been demonstrated on the ventricular cardiac sarcolemma of the rat (Ventura and colleagues (1989)). Similar studies have revealed δ- and κ-, but not μ-opioid receptors on rat atrial and ventricular tissue ( Krumins et al. (1985)). Developmental studies showed the presence of δ- and κ-opioid receptors in adult rat heart; whereas, only μ- and κ-opioid receptors were present in neonatal rat hearts (Zimlichman et al. (1996)). Additional evidence has been presented that δ- and κ-opioid receptors are present on canine cardiac sarcolemma and inhibit adenylate cyclase activity via activation of $G_i$ proteins (Mura and Niroomand (1996)). However, the role of the specific δ-opioid receptor subtype ($\delta_1$ and $\delta_2$) as well as a role for μ- and κ-opioid receptors in the cardioprotective effect of ischemic PC remains unknown.

Liu et al. (*Am. J. Physiol.* 1992: 263:(*Heart Circ. Physiol.* 32):H1107–H1112) has showed that ischemic PC protected against myocardial infarction and that this effect was mediated by adenosine A1 receptors in the rabbit. Gross and Auchampach (*Circ. Res*. 1992:70:223–233) were the first to demonstrate that preconditioning was mediated through the ATP-sensitive potassium ($K_{ATP}$) channel in the canine heart. In addition, $G_i$-proteins (Lasley et al. *J. Mol. Cell Cardiol.* 1993:25:815–821; Thornton et al. *J Mol. Cell Cardiol.* 1993:25:311–320) protein kinase C (PKC) (Ytrehus et al. *Am. J Physiol* 1994: 266:(*Heart Circ. Physiol.*):H1145–H1152), muscarinic receptors (Yao et al. *Am. J.*

*Physiol.* 1993: 264:(*Heart Circ. Physiol.* 34):H2221–H2225; Yao et al. *Circ. Res.* 1993:73:1193–1201), and the $Na^+/H^+$ exchanger (Bugge et al. *Basic Res. Cardiol.* 1996:91:203–209; Piper et al. *Basic Res. Cardiol.* 1996:91:191–202; Rohmann et al. *Cardiovasc. Res.* 1995:30:945–951) have been implicated in the mechanism(s) of ischemic PC. The two prominent, potential cardioprotective mechanisms, the adenosine A1 receptor and the $K_{ATP}$ channel, have also been investigated in the rat heart; however, Liu et al. (*Am. J. Physiol.* 1992: 263:(*Heart Circ. Physiol.* 32):H1107–H1112) found that neither mediator appeared to be responsible for ischemic PC in this species. Recently, the $K_{ATP}$ channel has been shown to mediate ischemic PC in the intact rat model of myocardial infarction (Qian et al. *Am. J. Physiol.*1996: 271:(*Heart Circ. Physiol.* 40):H23–H28; Schultz et al. *J. Mol. Cell Cardiol.* 1997:29:1055–1060; Schultz et al. *Am. J. Physiol.* 1997: 272:(*Heart Circ. Physiol.* 41):H2607–2615). Furthermore, stimulation of certain second messengers such as PKC (Li et al. *Am. J. Physiol.* 1995: 268:(*Heart Circ. Physiol.* 37):H426–431; Speechly-Dick et al. *Circ. Res.* 1994:75:586–590), heat stress proteins (Cox et al. In: Herz A., ed. *Handbook of Experimental Pharmacology: Opioids I.* New York: Springer-Verlag; 1993: 143–188) and muscarinic receptor activation (Qian et al. *Am. J. Physiol.* 1996: 271:(*Heart Circ. Physiol.* 40):H23–H28; Richard et al. *Br. J Pharmacol.* 1995:115:1532–1538) have been proposed to reduce myocardial necrosis in intact rats.

Recently, the Applicants have demonstrated that the opioid receptor system is involved in eliciting the cardioprotective effect of ischemic PC in the rat (Schultz et al. *J. Mol. Cell Cardiot.* 1997:29:2187–2195; Schultz et al. *J. Mol. Cell Cardiol.* 1997:29:1355–1362; Schultz et al. *Circ. Res.* 1996:78:1100–1104; Schultz et al.*J. Mol. Cell Cardiol.* 1997:29:A200; Schultz et al. *Am. J. Physiol.* 1995: 268: (*Heart Circ. Physiol.* 37):H2157–H2161). Applicants have shown that δ-opioid receptors, most notably the $\delta_1$-opioid receptor, mediate the cardioprotective effect of ischemic PC (Schultz et at. *J. Mol. Cell Cardiol.* 1997:29:2187–2195; Schultz et al. *J. Mol. Cell Cardiol.* 1997:29:A200). A number of investigators have provided evidence that Λ-opioid receptors exist on cardiac myocytes (Krumins et al. *Biochem. Biophys. Res. Comm.* 1985:127:120–128; Ventura et al. *Biochim. Biophys. Acta.* 1989:987:69–74; Ventura et al. *Circ. Res.* 1992:70:66–81; Zimlichman et al. *Circulation* 1996:93:1020–1025). In addition, Wittert and colleagues (Wittert et al. *Biochem. Biophys. Res. Comm.* 1996:218:877–881) determined the distribution of expression of the mu ($\mu$)-, kappa (κ)- and δ-opioid receptors in peripheral tissue of the rat and found that δ-receptor transcripts were predominantly detected in the heart; whereas, a weak $\mu$- and no κ-receptor transcripts were measured. Therefore, we tested the hypothesis that stimulating $\delta_1$-opioid receptors would reduce myocardial infarct size and that this opioid receptor-mediated cardioprotection involved a mechanism similar to that observed with ischemic PC in the rat heart (Schultz et al. *Am. J. Physiol.* 1998: 274:(*Heart Circ. Physiol.* 43):H909–H914).

DESCLOSURE OF THE INVENTION

The present invention is drawn to methods and pharmaceutical compositions for inducing protective effect of organs and tissues from ischemic damage. More specifically, the present invention is drawn to those organs or tissues having delta (δ) opioid receptors and even more specifically to those organs and tissues having delta-1 ($\delta_1$) opioid receptors.

A preferred embodiment of the present invention relates to methods for reducing ischemic damage to an organ having a delta (δ) opioid receptor and more specifically a delta-1 ($\delta_1$) opioid receptor in a mammal, by administering a therapeutically effective amount of an agonist to the delta (δ) opioid receptor or the delta-1 ($\delta^1$) opioid receptor in a suitable carrier. One preferred embodiment to the present invention relates to methods for reducing ischemic damage to an organ having a delta (δ) opioid receptor or more specifically a delta-1 ($\delta_1$) opioid receptor in humans, by administering a therapeutically effective amount of an agonist to the delta (δ) opioid receptor or the delta-1 ($\delta_1$) opioid receptor in a suitable carrier. Still another preferred embodiment of the present invention relates to such methods to reduce ischemic damage to the human heart. Preferred embodiments of the present invention contemplate methods to reduce ischemic damage to the human heart by administering a therapeutically effective amount of a delta-1 ($\delta_1$) opioid receptor agonist, such as any one of: (−)-2-Methyl-4aα-(3-hydroxyphenyl)-1,2,3,4,4a,5,12,12aβ-octahydroquinolino[2,3 g]isoquinoline (TAN67(−)), DPDPE, is [D-Pen2,D-Pen5]-enkephalin BW373U86 is (±)-4-((αR*)-α-((2S*,5R*)-4-allyl-2,5-dimethyl-1-piperazinyl)-3-hydroxybenzyl)-N,N-diethylbenzamide dihydrochloride; DADLE, is [D-Ala 2, D-Pen5]-enkephalin SB219825, is (−)-(4aS,8aS)-trans-2-[(Diethylamino)carbonyl]-6-ethyl-8a-(3-hydroxyphenyl)-3-methyl-4,4a,5,6,7,8,8a, 9-octahydro-1H-pyrrolo[2,3g]isoquinoline SNC80 is (+)-4-[(αR)-α-((2S,5R)-4-allyl-2,5-dimethyl-1-piperazinyl)-3-methoxybenzyl]-N,N-diethylbenzamide and SIOM is 7-spiroindanyloxymorphon. (−)-2-Methyl-4aα-(3-hydroxyphenyl)-1,2,3,4,4a,5,12,12aβ-octahydroquinolino [2,3 g]isoquinoline (TAN67(−)) has been disclosed in Japanese Laid Open Patent Application (Kokai) No. 4-275288, which is hereby incorporated by reference herein. SB219825, SNC80 and SIOM have been disclosed in J. Med. Chem., 1997, 40, 3192–3198, J. Med. Chem., 1994, 37, 2125–2128, and J. Med. Chem., 1993, 36, 2572–2574, respectively."

A still further preferred embodiment includes methods for reducing ischemic damage to an organ having a delta (δ) opioid receptor in a mammal, more specifically having a delta-1 ($\delta_1$) opioid receptor, and pharmaceutical compositions, wherein the agonist is represented by the formula:

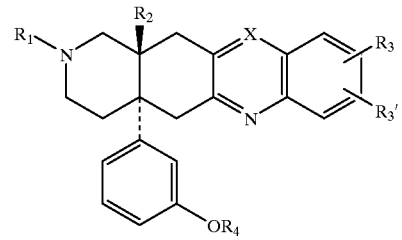

wherein $R_1$ represents a hydrogen atom, an alkyl group having 1–5 carbon atoms, a cycloalkylalkyl group having 4–7 carbon atoms, a cycloalkenylalkyl group having 5–7 carbon atoms, an aralkyl group having 7–14 carbon atoms, an alkenyl group having 4–5 carbon atoms, an allyl group, a furan-2-yl alkyl group, a thiophen-2-yl alkyl group, an alkanoyl group having 1–5 carbon atoms, a benzoyl group, a vinyloxycarbonyl group, a 2,2,2-trichloroethoxycarbonyl group, a benzyloxycarbonyl group, or an arylalkanoyl group having 8–14 carbon atoms;

$R_2$ represents a hydrogen atom or $OR_5$, wherein $R_5$ represents a hydrogen atom or an alkanoyl group having 1–5 carbon atoms;

$R_3$ and $R_3'$ each independently represents a hydrogen atom, an alkyl group having 1–5 carbon atoms, fluorine, chlorine, bromine, iodine, an alkoxy group having 1–5 carbon atoms, a nitro group, an amino group, or an alkylamino group;

$R_4$ represents a hydrogen atom, an alkyl group having 1–3 carbon atoms, a benzyl group, or an alkanoyl group having 1–5 carbon atoms; and X represents CH or N.

More preferred embodiment includes methods for reducing ischemic damage to an organ having a delta ($\delta$) opioid receptor in a mammal, more specifically having a delta-1 ($\delta$) opioid receptor, and pharmaceutical compositions wherein in said formula $R_1$ is an alkyl group having 1–5 carbon atoms, a cycloalkylalkyl group having 4–7 carbon atoms, an aralkyl group having 7–14 carbon atoms, an alkenyl group having 4–5 carbon atoms, or an allyl group. These compounds represented by said formula and substitutions as contemplated by the present invention and processes for producing same have been disclosed in Japanese Laid Open Patent Application (Kokai) No. 4-275288, which is hereby incorporated by reference herein.

The present invention further contemplates administration of such agonists in a number of medically acceptable fashions, including, for example: in injectable form; by mouth; or in a cardioplegic solution. Wherein a cardioplegic solution means a solution administered in conjunction with or during cardioplegia or a cardioplegic procedure. The skilled artisan would readily understand that cardioplegia or a cardioplegic procedure refers to a paralysis of the heart, as performed during an elective stopping of the heart using chemicals, selective hypothermia or electrical stimulation.

Another preferred embodiment of the present invention relates to methods for inducing cardioprotective effect in mammals, including humans, by administering a therapeutically effective amount of a delta ($\delta$) opioid receptor agonist or more specifically a delta-1 ($\delta$) opioid receptor agonist in a suitable carrier. Such agonists include the compounds represented by the formula:

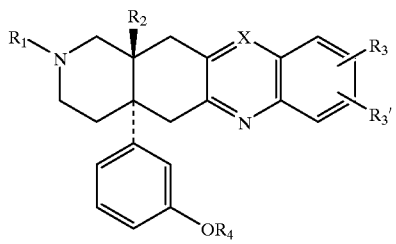

wherein $R_1$ represents a hydrogen atom, an alkyl group having 1–5 carbon atoms, a cycloalkylalkyl group having 4–7 carbon atoms, a cycloalkenylalkyl group having 5–7 carbon atoms, an aralkyl group having 7–14 carbon atoms, an alkenyl group having 4–5 carbon atoms, an allyl group, a furan-2-yl alkyl group, a thiophen-2-yl alkyl group, an alkanoyl group having 1–5 carbon atoms, a benzoyl group, a vinyloxycarbonyl group, a 2,2,2-trichloroethoxycarbonyl group, a benzyloxycarbonyl group, or an arylalkanoyl group having 8–14 carbon atoms;

$R_2$ represents a hydrogen atom or $OR_5$, wherein $R_5$ represents a hydrogen atom or an alkanoyl group having 1–5 carbon atoms;

$R_3$ and $R_3'$ each independently represents a hydrogen atom, an alkyl group having 1–5 carbon atoms, fluorine, chlorine, bromine, iodine, an alkoxy group having 1–5 carbon atoms, a nitro group, an amino group, or an alkylamino group;

$R_4$ represents a hydrogen atom, an alkyl group having 1–3 carbon atoms, a benzyl group, or an alkanoyl group having 1–5 carbon atoms; and X represents CH or N.

The agonist represented by the formula, wherein $R_1$ is an alkyl group having 1–5 carbon atoms, a cycloalkylalkyl group having 4–7 carbon atoms, an aralkyl group having 7–14 carbon atoms, an alkenyl group having 4–5 carbon atoms, or an allyl group, is more preferable.

$\delta_1$ opioid receptor agonists include, for example, any one of: TAN67(-), DPDPE, BW 373U86, DADLE, SB219825, SNC80 and SIOM, which could be administered in a number of medically acceptable ways such as: in injectable form; in form for oral administration; or in a cardioplegic solution.

Still another preferred embodiment of the present invention relates to pharmaceutical compositions of matter containing a therapeutically effective amount of a delta ($\delta$) opioid receptor agonist or more specifically a delta-1 ($\delta_1$) opioid receptor agonist in a suitable carrier, for inducing cardioprotective effect in human patients. Such agonists include the compounds represented by the formula:

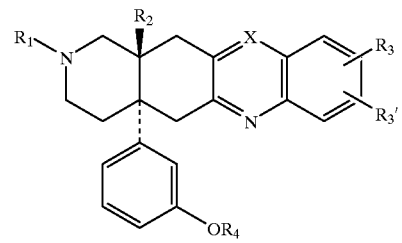

wherein $R_1$ represents a hydrogen atom, an alkyl group having 1–5 carbon atoms, a cycloalkylalkyl group having 4–7 carbon atoms, a cycloalkenylalkyl group having 5–7 carbon atoms, an aralkyl group having 7–14 carbon atoms, an alkenyl group having 4–5 carbon atoms, an allyl group, a furan-2-yl alkyl group, a thiophen-2-yl alkyl group, an alkanoyl group having 1–5 carbon atoms, a benzoyl group, a vinyloxycarbonyl group, a 2,2,2-trichloroethoxycarbonyl group, a benzyloxycarbonyl group, or an arylalkanoyl group having 8–14 carbon atoms;

$R_2$ represents a hydrogen atom or $OR_5$, wherein $R_5$ represents a hydrogen atom or an alkanoyl group having 1–5 carbon atoms;

$R_3$ and $R_3'$ each independently represents a hydrogen atom, an alkyl group having 1–5 carbon atoms, fluorine, chlorine, bromine, iodine, an alkoxy group having 1–5 carbon atoms, a nitro group, an amino group, or an alkylamino group;

$R_4$ represents a hydrogen atom, an alkyl group having 1–3 carbon atoms, a benzyl group, or an alkanoyl group having 1–5 carbon atoms; and X represents CH or N.

The agonist represented by the formula, wherein $R_1$ is an alkyl group having 1–5 carbon atoms, a cycloalkylalkyl group having 4–7 carbon atoms, an aralkyl group having 7–14 carbon atoms, an alkenyl group having 4–5 carbon atoms, or an allyl group, is more preferable.

Such agonists, include, for example, any one of: TAN67 (−), DPDPE, BW 373U86, DADLE, SB219825, SNC80 and SIOM. These pharmaceutical compositions may be formulated in a number of medically acceptable ways, including, for example: in injectable form; in form for oral administration or in a suitable carrier solution for cardioplegic administration.

Another embodiment of the present invention includes methods for blocking ischemic preconditioning (PC) by administering a therapeutically effective amount of a delta ($\delta$) opioid receptor antagonist or more specifically a delta-1 ($\delta_1$) opioid receptor antagonist in a suitable carrier. Such antagonists include, for example: 7-benzylidenenaltrexone (BNTX), and naloxone.

BRIEF DESCRIPTION OF THE DRAWINGS

FIG. 1. Protocol used to determine which $\delta$-opioid receptor subtype mediates the cardioprotective effect of ischemic PC.

FIG. 2. Protocol to demonstrate a role of $\mu$- and $\kappa$-opioid receptors in ischemic PC.

FIG. 3. Infarct sizes in rat hearts subjected to control (CON), ischemic preconditioning (PC) elicited by three 5 minute occlusion periods interspersed with 5 minutes of reperfusion; BNTX (3 mg/kg, iv), a selective $\delta_1$-opioid receptor antagonist, given 10 minutes before the 30 minutes of occlusion; low BNTX+PC, BNTX (1 mg/kg, iv) given 10 minutes before ischemic PC; and hi BNTX+PC, BNTX (3 mg/kg, iv) given 10 minutes before ischemic PC. Open circles indicate the infarct sizes from individual hearts. Filled circles in each group indicate the group mean infarct size; mean ±S.E.M. with a *p<0.05 vs control and *§p<0.05 vs control and ischemic PC.

FIG. 4. Infarct sizes in rat hearts subjected to control (CON); ischemic preconditioning (PC) elicited by three 5 minute occlusion periods interspersed with 5 minutes of reperfusion; NTB, naltriben (1 mg/kg, iv), a $\delta_2$-opioid receptor antagonist, given 10 minutes before the 30 minutes of occlusion; low NTB+PC, NTB (1 mg/kg, iv) given 10 minutes before ischemic PC; and hi NTB+PC, naltriben (3 mg/kg, iv) infused for 60 minutes before ischemic PC. Open circles indicate the infarct sizes from individual hearts. Filled circles in each group indicate the group mean infarct size; mean ±S.E.M. with a *p<0.05 vs control.

MODES OF CARRYING OUT THE INVENTION

Figure 5:
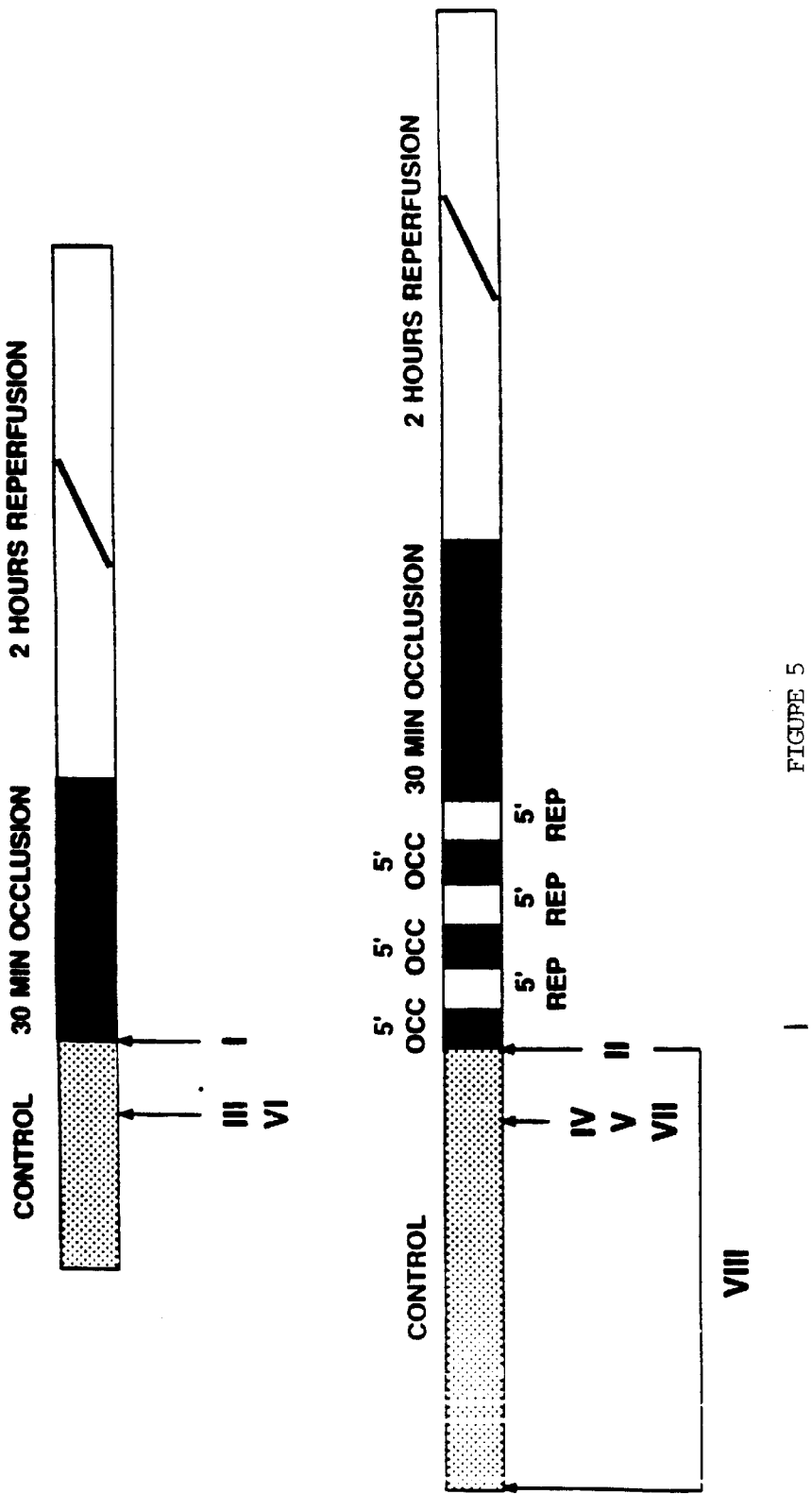
FIG. 5. Infarct sizes in rat hearts subjected to control (CON), 3×5 minute ischemic preconditioning (PC), $\beta$-funaltrexamine (15 mg/kg, sc), an irreversible $\mu$- opioid receptor antagonist, given 24 hours before ischemic PC ($\beta$-FNA+PC), DAMGO, a $\mu$-opioid receptor agonist, given as 3×5 minute DAMGO infusions (3×1 mg/kg/infusion, low DAMGO; 3×10 mg/kg/infusion, med DAMGO; and 3×100 mg/kg/infusion, hi DAMGO). Open circles indicate infarct sizes from individual hearts. Filled circles in each group indicate the average infarct size, mean ISEM with *p<0.05 vs control.

Embodiments of this invention relate to administering compounds that preferentially or specifically bind to opioid receptors, specifically delta ($\delta$) opioid receptors and more specifically delta-1 ($\delta_1$) opioid receptors. Such compounds that preferentially or specifically bind to said receptors may be agonists or antagonists. Agonist compounds are characterized as those compounds that upon binding to delta ($\delta$) opioid receptors or delta-1 ($\delta_1$) opioid receptors result in a physiological response that mimics that associated with the binding of endogenous opioid compounds to delta ($\delta$) opioid receptors or delta-1 ($\delta_1$) opioid receptors. Antagonist compounds are those that upon binding to delta ($\delta$) opioid receptors or delta-1 ($\delta_1$) opioid receptors result in the inhibition or prevention of the physiological response associated with the binding of opioid compounds to delta ($\delta$) opioid receptors or delta-1 ($\delta_1$) opioid receptors.

Those of ordinary skill in the art would readily be able to select agonists or antagonists that bind to delta ($\delta$) opioid receptors or delta-1 ($\delta_1$) opioid receptors. The class of delta ($\delta$) opioid receptors consists of two subtypes, $\delta_1$ and $\delta_2$, see Jiang, Q., et al., *J Pharmacol Exp Ther* (1991) 257:1069–1075; Mattia, A., et al., *J Pharmacol Exp Ther* (1991) 258:583–587; and Sofuoglu, M., et al., *J Pharmacol*

*Exp Ther* (1991) 257:676–680. For example, there are a number of pharmacological agents available to distinguish these two subtypes of delta (δ) opioid receptor (Dhawan, B. N., et al., *Pharmacol Rev* (1996) 48:567–592). 7-benzylidenenaltrexone (BNTX), a nonpeptidic $δ_1$-opioid receptor antagonist, and naltriben (NTB), a nonpeptidic $δ_2$-opioid receptor antagonist, were used in the present invention to clarify the role of these two subtypes to mediate the cardioprotective effect of ischemic PC. A number of prior studies have demonstrated the selectivity and specificity of BNTX and NTB towards its respective opioid receptor. Portoghese, P. S., et al., *Eur J Pharmacol* (1992) 218:195–196; Ttakemori, A. E., et al., *Life Sci* (1992) 50:149–1495, and Sofuoglu, M. et al., *Life Sci* (1993) 52:769–775. The present invention demonstrates a dose response of both BNTX and NTB (see: FIGS. 3 and 4). The results demonstrate that the high dose (3 mg/kg, iv) of BNTX but not the low dose (1 mg/kg, iv) partially abolished the protective effect of ischemic PC; whereas, neither dose of NTB (1 or 3 mg/kg, iv) blocked ischemic PC. BNTX (3 mg/kg, iv) and NTB (1 mg/kg, iv) administered in combination 10 minutes before ischemic PC did not have an additive effect to block the cardioprotective effect (data not shown). In fact, the IS observed when the combination of BNTX and NTB were given together was no larger than the IS observed when BNTX alone was given before ischemic PC which further suggests that ischemic PC in the rat heart is predominantly mediated via the delta-1 ($δ_1$) opioid receptor. Overall, these data demonstrate that the delta-1 ($δ_1$) opioid receptor is the important delta (δ) opioid receptor subtype involved in the cardioprotective effect of ischemic PC in the rat. Those of ordinary skill in the art would readily be able to apply these studies to other organs and tissues in other mammalian species.

Further, confirmation of the role of the delta (δ) opioid receptors and more specifically the delta-1 ($δ_1$) opioid receptors and not the μ- or κ-opioid receptor in PC is supported by studies using the L-receptor agonist, DAMGO and the irreversible μ-receptor antagonist, β-funaltrexamine (β-FNA) and the κ-receptor antagonist, nor-binaltorphimine (nor-BNI). Many studies have provided evidence that DAMGO and β-FNA are selective for the μ-opioid receptor, Takemori, A. E., et al., *Eur J Pharmacol* (1981) 70:445–451 and Ward, S. J., et al., *J Pharmacol Exp Ther* (1982) 220:494–498 and nor-BNI is selective for κ-opioid receptors. Portoghese, P. S., et al., *J Med Chem* (1987) 30:238–239 and *Life Sci* (1987) 40:1287–1292. It has been shown that β-FNA (15 mg/kg, sc) when administered 24 hours preceding ischemic PC did not block its cardioprotective effect. Similarly, DAMGO at any of the doses studied did not mimic the cardioprotection induced by brief periods of ischemia. These results clearly show that the μ-opioid receptor does not mediate ischemic PC. The lack of μ-opioid receptor activity in the cardioprotective effect of ischemic PC has been supported by a number of receptor binding studies in ventricular myocytes indicating an absence of this particular opioid receptor in this tissue. Krumins, S. A., et al., *Biochem Biophys Res Comm* (1985) 127:120–128 and Ventura, C. et al., *Biochim Biophys Acta* (1989) 987:69–74. In addition, the hypoxic conditioning study by Mayfield, et al and D'Alecy, et al., showed that β-FNA (48 hour pretreatment with 1–20 mg/kg, sc) did not decrease hypoxic survival time in mice indicating that the μ-opioid receptor was not involved.

Figure 7:
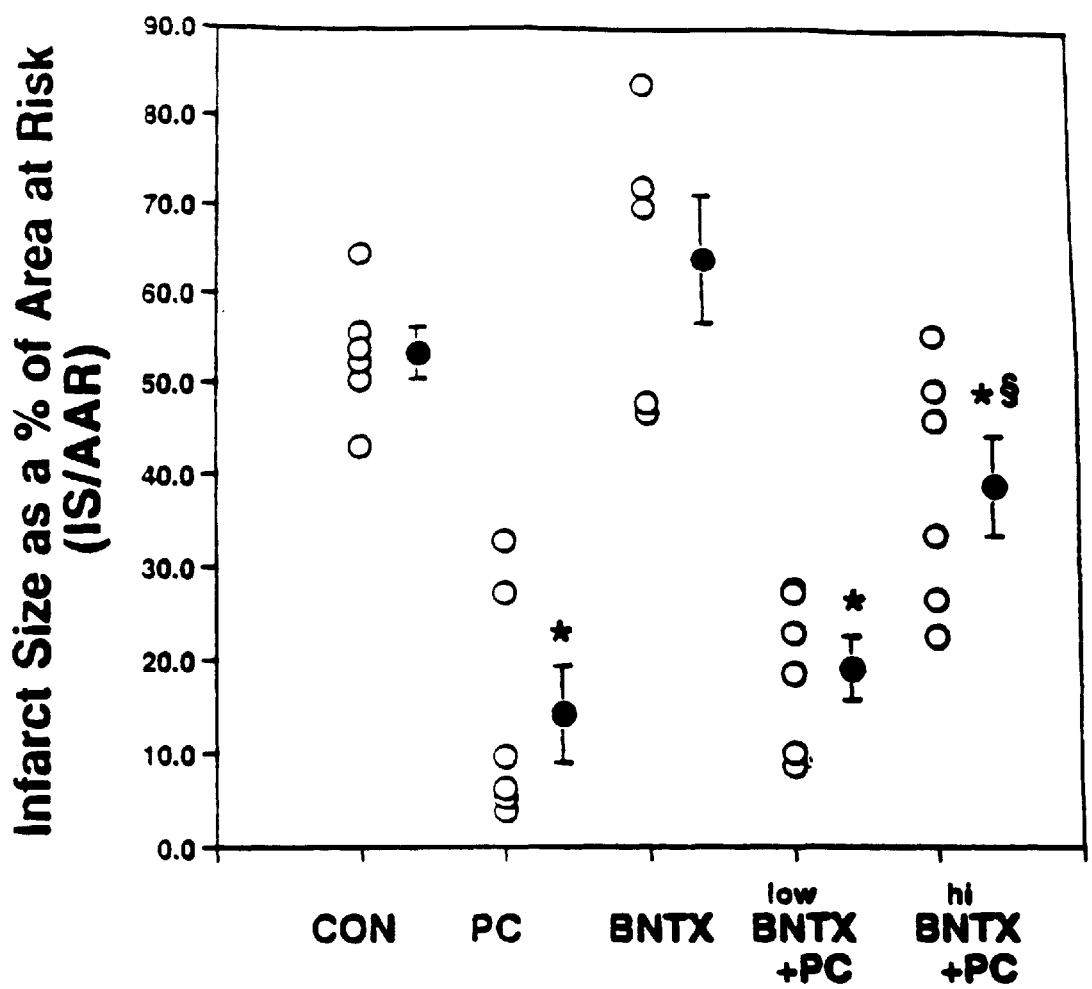
FIG. 7. Vascular effect of DAMGO, $\mu$-opioid receptor agonist, and the change in mean arterial blood pressure responses during administration of selective $\mu$- and $\delta$-opioid receptor antagonists. DAMGO produced a dose-dependent (3–300 mg/kg, iv) decrease in MBP (closed circles). $\beta$-FNA, the irreversible $\mu$-opioid receptor antagonist, completely abolished the hypotension induced by DAMGO (closed squares; *p<0.05). Neither BNTX, the $\delta_1$-opioid receptor antagonist, nor NTB, the $\delta_2$-opioid receptor antagonist, blocked the decrease in MBP produced by DAMGO (open triangles and open squares, respectively).

The selectivity of DAMGO to the μ- opioid receptor was studied against β-FNA, BNTX, and NTB. A transient hypotension was observed during infusion of DAMGO and this physiological response was used as the parameter to study the selectivity of the opioid agonist and antagonists. Twenty-four hour pretreatment with β-FNA blocked the DAMGO-induced hypotension; whereas, neither BNTX nor NTB inhibited the transient hypotension which occurred during DAMGO infusion (FIG. 7). In addition, the specificity of BNTX to the delta-1 ($δ_1$) opioid receptor was tested against DPDPE, the delta-1 ($δ_1$) opioid receptor agonist. BNTX antagonized the DPDPE-induced decrease in blood pressure. These results demonstrate that the doses of the μ- and delta (δ) opioid receptor agents were selective for their respective opioid receptors.

The role of κ-opioid receptors in the protective effect of ischemic PC was tested by the use of nor-BNI, a selective κ-opioid receptor antagonist. A dose response of nor-BNI (1 and 5 mg/kg, iv) was performed. Neither dose of nor-BNI antagonized ischemic PC suggesting that κ-opioid receptors are not involved in cardioprotection in the rat. As with the BNTX and NTB combination, there was no additive effect to block ischemic PC in the rat when BNTX (3 mg/kg, iv) and nor-BNI (1 mg/kg, iv) were given together (data not shown). In support of the lack of involvement of the κ-opioid receptor in ischemic PC (Xia, et al. (Xia, Q, et al. *Life Sci* (1996) 58:1307–1313) demonstrated that antiarrhythmic effect of ischemic PC in the isolated rat heart may be due to a decreased affinity of κ-opioid receptor binding by U69593, a highly selective κ-agonist, during reperfusion. Also, Mayfield, K. P. et al., *J Pharmacol Exp Ther* (1994) 268:74–77) were unable to decrease hypoxic survival time of mice with nor-BNI (1–20 mg/kg, sc) when animals were subjected to hypoxic preconditioning. Furthermore, Niroomand F., et al., *Naunyn-Schmiedeberg's Arch Pharmacol* (1996) 354:643–649 indicated that κ-opioid receptors may not be present on canine cardiac sarcolemma since the κ-agonist, U50488H, did not inhibit adenylate cyclase activity.

One of ordinary skill in the art following the disclosure of the present invention would readily be able to select those delta-1 ($δ_1$) opioid receptor agonists that provide a protective effect of ischemic PC as performed by the role of $K_{ATP}$ channels and $G_{i/o}$ proteins which mediate ischemic PC and result in the cardioprotective effect produced by delta-1 ($δ_1$) opioid receptor activation. For example, a determination of infarct size and a statistical analysis of the data were conducted in which the average IS/AAR for the control group was 55.6±2.1%. A 15 minute infusion period of TAN67(−) (10 mg/kg, iv), the nonpeptidic $δ_1$-opioid receptor agonist, significantly reduced infarct size as compared to the control group (27.1±4.8%, *p<0.05). The cardioprotection induced by TAN67(−) was completely abolished by BNTX (3 mg/kg, iv), a selective $δ_1$-opioid receptor antagonist, indicating that TAN produces its cardioprotective effect via $δ_1$-opioid receptors. Furthermore, $δ_1$-opioid receptor-induced cardioprotection appears to be mediated via the $K_{ATP}$ channel since glibenclamide (0.3 mg/kg, iv) administered 45 minutes before the TAN67(−) infusion completely blocked the cardioprotection (53.0±5.4%. GLY+ TAN). A role for $G_{i/o}$ proteins was also shown to be involved in the cardioprotective effect of TAN67(−) since a 48 hour pretreatment with pertussis toxin (10 μg/kg, ip), an inhibitor of $G_{i/o}$ proteins, abolished the cardioprotective effect induced by TAN67(−) (60.8±3.6%; PTX+TAN).

In summary, these results indicate that the beneficial effect of brief periods of ischemia are mediated via delta (δ) opioid receptors and more specifically by the delta-1 ($δ_1$) opioid receptor. BNTX, the delta-1 ($δ_1$)-opioid receptor antagonist, blocked the cardioprotection; whereas, NTB, the delta-2

($\delta_2$)-opioid receptor antagonist, did not inhibit ischemic PC. Neither $\mu$ or $\kappa$-opioid receptors seem to be involved in eliciting cardioprotection in the rat heart since antagonists to these two receptors did not prevent PC and DAMGO, a $\mu$-opioid receptor agonist did not mimic ischemic PC. Also, combinations of the delta-2 ($\delta_2$) opioid receptor or $\kappa$-antagonist with BNTX did not produce an additive inhibition of ischemic PC in comparison to the results with BNTX alone suggesting that ischemic PC in the rat occurs via activation of delta-1 ($\delta_1$)-opioid receptors. This invention has important clinical ramifications with regard to pain, cardiac ischemia and coronary artery disease. Opioids have been used clinically to manage pain post-operatively. The demonstration that opioid receptors, most notably delta-1 ($\delta_1$) opioid receptors, which not only have analgesic properties but may have the potential to protect the myocardium during cardiac surgical interventions suggests a possible new pharmacological approach for the treatment of patients suffering from an acute myocardial infarction.

Specifically, one preferred embodiment of this invention relates to a method for reducing in a patient ischemic damage to an organ having a delta ($\delta$) opioid receptor and more specifically a delta-1 ($\delta_1$) opioid receptor, by administering to the patient a therapeutically effective amount of an agonist to the delta ($\delta$) opioid receptor or the delta-1 ($\delta_1$) opioid receptor in a suitable carrier. More specifically, a preferred embodiment of this invention relates to a method for reducing in a patient ischemic damage to the heart, by administering to the patient a therapeutically effective amount of an agonist to a delta ($\delta$) opioid receptor and more specifically a delta-1 ($\delta_1$) opioid receptor in a suitable carrier. One of ordinary skill in-the art would readily be able to select a suitable agonist and would readily understand that such agonists include, but are not limited to, TAN67(−), DPDPE, BW 373U86, DADLE, SB219825, SNC80 and SIOM.

Another preferred embodiment of this invention relates to pharmaceutical compositions of matter for reducing in a patient ischemic damage to an organ having a delta ($\delta$) opioid receptor and more specifically a delta-1 ($\delta_1$) opioid receptor, comprising a therapeutically effective amount of a delta ($\delta$) opioid receptor agonist and more specifically a delta-1 ($\delta_1$) opioid receptor agonist in a suitable carreir. More specifically, a preferred embodiment of this invention relates to pharmaceutical compositions for reducing in a patient ischemic damage to the heart, comprising a therapeutically effective amount of a delta ($\delta$) opioid receptor agonist and more specifically a delta-1 ($\delta_1$) opioid receptor agonist in a suitable carrier. One of ordinary skill in the art would readily be able to select a suitable agonist and would readily understand that such agonists include, but are not limited to, TAN67(−), DPDPE, BW373W86, DADLE, SB219825, SNC80 and SIOM.

The diseases relating to ischemic damage to the heart are, for example, angina pectoris, unstable angina pectoris, angina pectoris after myocardial infarction, myocardial infarction, acute myocardial infarction, coronary restenosis after PTCA.

Another preferred embodiment of this invention relates to a method for inducing a cardioprotective effect by administering a therapeutically effective amount of a delta ($\delta$) opioid receptor agonist and more specifically a delta-1 ($\delta_1$) opioid receptor agonist in a suitable carrier. One of ordinary skill in the art would readily be able to select a suitable agonist and would readily understand that such agonists include, but are not limited to, TAN67(−), DPDPE, BW 373U86, DADLE, SB219825, SNC80 and SIOM.

Another preferred embodiment of this invention relates to pharmaceutical compositions of matter for inducing cardioprotective effect, comprising a therapeutically effective amount of a delta ($\delta$) opioid receptor agonist and more specifically a delta-1 ($\delta_1$) opioid receptor agonist in a suitable carrier. One of ordinary skill in the art would readily be able to select a suitable agonist and would readily understand that such agonists include, but are not limited to, TAN67(−), DPDPE, BW 373U86, DADLE, SB219825, SNC80 and SIOM.

Another preferred embodiment of this invention relates to a method for inducing in a human patient a cardioprotective effect by administering a therapeutically effective amount of a delta ($\delta$) opioid receptor agonist and more specifically a delta-1 ($\delta_1$) opioid receptor agonist in a suitable carrier. One of ordinary skill in the art would readily be able to select a suitable agonist and would readily understand that such agonists include, but are not limited to, TAN67(−), DPDPE, BW 373U86, DADLE, SB219825, SNC80 and SIOM.

The diseases applied for cardioprotection are, for example, angina pectoris, unstable angina pectoris, anginapectoris after myocardial infarction, myocardial infarction, acute myocardial infarction and coronary restenosis after PTCA.

Similarly, in some instances, it may be preferable and medically indicated to block ischemic preconditioning (PC). Another embodiment of this invention relates to blocking ischemic preconditioning (PC) by administering a therapeutically effective amount of a receptor antagonist in a suitable carrier, specifically, such antagonist would include an opioid receptor antagonist. More specifically, an embodiment of this invention relates to blocking ischemic preconditioning (PC) by the administration of a delta ($\delta$) opioid receptor antagonist, specifically, a delta-1 ($\delta_1$) opioid receptor antagonist. One of ordinary skill in the art would readily be able to select a suitable antagonist and would readily understand that such antagonists include, but are not limited to 7-benzylidenenaltrexone (BNTX).

Another embodiment of this invention relates to pharmaceutical compositions used to block ischemic preconditioning (PC) by administering a therapeutically effective amount of a receptor antagonist in a suitable carrier, specifically, an antagonist to an opioid receptor. More specifically, an embodiment of this invention relates to pharmaceutical compositions used to block ischemic preconditioning (PC) by administering a therapeutically effective amount of a delta ($\delta$) opioid receptor antagonist and even more specifically, a delta-1 ($\delta_1$) opioid receptor antagonist.

Another embodiment of this invention relates to the administration of a cardioplegic solution containing an effective amount of a delta ($\delta$) opioid receptor agonist and more specifically a delta-1 ($\delta_1$) opioid receptor agonist during open heart surgery to induce cardioprotective effect.

The form of administration may be, for example, as an injection; an oral preparation such as tablets, capsules, granules, powder or syrup. A pharmaceutical composition of the present invention preferably contains the effective component in an amount of 0.00001 to 90 wt %, and more preferably 0.0001 to 70 wt %. The dosages are appropriately selected depending on factors such as symptoms, age, body weight and method of administration, but in the case of injection for adults, 0.001 to 1.0 g may be administered per day, either at once or spread over several administrations.

The following examples are intended to illustrate but not to limit the invention.

EXAMPLE 1

General Surgical Preparation

Male Wistar rats weighing 350–450 grams were used. The rats were anesthetized by intraperitoneal administration with the long-acting thiobutabarbital, inactin (100 mg/kg, iv). A tracheotomy was performed and the rat was intubated with a cannula connected to a rodent ventilator (model 683, Harvard Apparatus, South Natick, Mass., USA) and ventilated with room air at 65–70 breaths/min. Atelectasis was prevented by maintaining a positive end-expiratory pressure of 5–10 mm of $H_2O$. Arterial pH, $P_{CO_2}$, and $P_{O_2}$ were monitored at baseline, 15 minutes of occlusion, and at 15, 60, and 120 minutes of reperfusion by a blood gas system (AVL 995, Automatic Blood Gas System, Rosewell, GA, USA) and maintained within a normal physiological range (pH 7.35–7.45; $P_{CO_2}$ 25–40 mmHg; $P_{O_2}$ 80–110 mmHg) by adjusting the respiratory rate and/or tidal volume. Body temperature was monitored (Yellow Springs Instruments Tele-Thermometer, Yellow Springs, OH, USA) and maintained at 37±1° C. (mean±SEM) by using a heating pad.

The right carotid artery was cannulated to measure blood pressure and heart rate via a Gould PE50 or Gould PE23 pressure transducer which was connected to a Grass (Model 7) polygraph. The right jugular vein was cannulated to infuse saline or drugs. A left thoracotomy was performed approximately 15–20 mm from the sternum to expose the heart at the fifth intercostal space. The pericardium was removed and the left atrial appendage was moved to reveal the location of the left coronary artery. The vein descending along the septum of the heart was used as the marker for the left coronary artery. A ligature (6–0 prolene), along with a snare occluder, was placed around the vein and left coronary artery close to the place of origin. Following surgical preparation, the rat was allowed to stabilize for 15 minutes prior to the various interventions.

Drugs

Inactin, (−)-trans-(1S,2S)-U-50488H, nor-binaltorphimine (nor-BNI), pertussis toxin (PTX) and [D-Pen², D-Pen⁵]-enkephalin (DPDPE) were purchased from Research Biochemicals International, Natick, Mass., USA. (−)-2-Methyl-4a α-(3-hydroxyphenyl)-1,2,3,4,4a,5,12,12a β-octahydroquinolino[2,3-g]isoquinoline (TAN67 (−)) (See, Japanese Laid Open Patent Application (Kokai) No. 4-275288, which is hereby incorporated by reference herein), 7-benzylidenenaltrexone (BNTX), naltriben (NTB), and β-funaltrexamine(β-FNA) were generously donated as gifts from Toray Industries, Inc., Kanagawa, Japan. D-Ala², N-Me-Phe⁴,glycerol⁵-enkephalin (DAMGO) was purchased from Bachem Bioscience, Inc., King of Prussia, Pa., USA. 2,3,5-triphenyltetrazolium chloride (TTC) was purchased from Sigma Chemical Co. Inactin, NTB, and DAMGO were dissolved in 0.9% saline. BNTX and DPDPE were dissolved in distilled water and brought up to volume with saline. β-FNA, U-50488H, and nor-BNI were dissolved in distilled water. Glibenclamide was dissolved in a 1:1:1:2 cocktail mixture of polyethylene glycol (PEG), 95% ethanol, 0.1 N sodium hydroxide and 0.9% saline, respectively. We have previously shown that saline or glibenclamide vehicle has no effect on infarct size in nonpreconditioned rat hearts (Schultz et al. Circ. Res. 1996:78:1100–1104). TTC was dissolved in a 100 mmol/L phosphate buffer.

Study Groups and Experimental Protocols

All protocols contained control (group 1) and 3×5 minute ischemic PC (group II) groups. The control group was subjected to 30 minutes of occlusion and 2 hours of reperfusion. Ischemic PC was elicited by 3×5 minute occlusion periods interspersed with 5 minutes of reperfusion prior to the prolonged occlusion and reperfusions periods. FIG. 1 represents the experimental protocol designed to demonstrate the specific δ($δ_1$ or $δ_2$)-opioid receptor involved in the cardioprotective effect of ischemic PC. In group III, BNTX (3 mg/kg, iv) was given 10 minutes before the long occlusion period in nonpreconditioned animals. Groups IV and V showed a dose response effect of BNTX to antagonize ischemic PC (1 and 3 mg/kg, iv; lowBNTX+PC and hiBNTX+PC, respectively). In group VI, NTB (1mg/kg, iv) was administered 10 minutes before the 30 minutes of occlusion in nonpreconditioned animals. In groups VII and VIII, NTB (1 and 3 mg/kg, iv, respectively) was given 10 minutes or as a 60 minute infusion before ischemic PC (lowNTB+PC and hiNTB+PC, respectively).

Furthermore, μ- and κ-opioid receptors have been implicated in many cardiovascular physiological and pathophysiological responses (Holaday, J .W., Ann Rev Pharmacol Toxicol (1983) 23:541–594; Martin, W. R., Pharmacol Rev (1983) 35:283–323; Wong, T. M. et al. J Mol Cell Cardiol (1990) 22:1167–1175; Siren, A-L, et al. News Physiol Sci (1992) 7:26–30). Therefore, pharmacological antagonists and one agonist were used to determine if these two opioid receptors were involved in ischemic PC in the intact rat heart (FIG. 2). In group IX, animals were pretreated 24 hours prior to ischemic PC with β-funaltrexamine (β-FNA; 15 mg/kg, sc), an irreversible μ-opioid receptor antagonist (β-FNA+PC). To test if stimulating the μ-opioid receptor mimicked ischemic PC, groups X-XII consisted of 3×5 minute infusions (1, 10 and 100 mg/kg/infusion, iv, respectively) of DAMGO, a selective μ-opioid receptor agonist, interspersed with 5 minutes of no drug infusion prior to the prolonged ischemic and reperfusion periods (lowDAMGO, medDAMGO, hiDAMGO, respectively). Lastly, to test if κ-opioid receptors mediated the cardioprotective effect of ischemic PC, a dose response effect of nor-BNI, a k-opioid receptor antagonist, to block ischemic PC was studied. In groups XIII (lownor-BNI+PC) and XIV (hinor-BNI+PC), nor-BNI (1 and 5 mg/kg, iv, respectively) was given 15 minutes before ischemic PC.

To demonstrate that the effect of the antagonists and agonists occurred at a specific opioid receptor, BNTX, and NTB, the $δ_1$- and $δ_2$-opioid receptor antagonists, respectively, β-FNA, the irreversible μ-opioid receptor antagonist, DAMGO, the μ-opioid receptor agonist, DPDPE, the delta-1 ($δ_1$) opioid receptor agonist, and U-50488H, a k-opioid receptor agonist, were utilized. DAMGO produced a transient hypotensive effect during the three doses (3×1, 10, 100 mg/kg/infusion, iv) studied. Therefore, animals which were pretreated with β-FNA (group IX from FIG. 2) were subjected to a dose response of DAMGO (3, 30, 300 mg/kg, iv) prior to ischemic PC to test the specificity of β-FNA for the μ-opioid receptor. Similarly, a dose response of DAMGO (3, 30, 300 mg/kg, iv) was studied with BNTX or NTB (groups III and VI from FIG. 1) in which either delta (δ) opioid receptor antagonist was given and then a DAMGO dose response was performed before the long occlusion period to demonstrate the specificity of the $δ_1$-(BNTX) and $δ_2$-(NTB) opioid receptor antagonists. In addition, specificity of the $δ_1$-, $δ_2$-, and k-antagonists to their respective opioid receptors were demonstrated using a δ- and k-opioid receptor agonist. A dose response of DPDPE (1, 3, and 10 mg/kg, iv), the delta-1 ($δ_1$) opioid receptor agonist, was performed and a transient decrease in blood pressure was observed. BNTX (3 mg/kg, iv), the $δ_1$-opioid receptor antagonist, was given 10 minutes before the next DPDPE dose response. Similarly, a dose response of U-50488H (1, 5, and 10 mg/kg, iv), the k-opioid receptor agonist, was performed followed by the administration of nor-BNI (5 mg/kg, iv), the k-opioid receptor antagonist, 15 minutes before the next U-50488H dose response.

Determination of Infarct Size

After each experiment, the left coronary artery was reoccluded and Patent blue dye was injected into the venous catheter to stain the normally perfused region of the heart. The rat was euthanized with 15% KCl through the arterial catheter. The heart was excised and the left ventricle removed and sliced into five cross-sectional pieces. This procedure allowed for visualization of the normal, nonischemic region and the area at risk (AAR). The AAR was separated from the normal area using a dissecting scope (Cambridge Instruments). Both tissue regions (nonischemic and AAR) were incubated at 37° C. for 15 minutes in a 1% 2,3,5-triphenyltetrazolium stain in 100 mmol/L phosphate buffer (pH 7.4). TTC was used as an indicator to separate out viable and nonviable tissue (Klein, H. H., et al., Virchows Arch (1981) 393:287–297). The tissue was stored overnight in a 10% formaldehyde solution. The following day, the infarcted tissue was separated from the AAR by using a dissecting scope. The different regions (nonischemic, AAR, and infarct) were determined by gravimetry and infarct size (IS) was calculated as a % of the AAR (IS/AAR).

Exclusion Criteria

A total of 107 animals were assigned to the present study. Animals were excluded from the study because of unacceptable blood gases, intractable ventricular fibrillation (VF) or hypotension (mean arterial blood pressure below 30 mmHg). Three animals in the control group, two in the ischemic PC group, two animals in the hiBNTX+PC group, one in the hiDAMGO group, and four animals in the b-FNA+PC group were excluded due to intractable ventricular fibrillation. In addition, three animals in the hiNTB+PC group and one animal in the lownor-BNI+PC group were excluded due to hypotension. A total of 91 animals completed the study.

Statistical Analysis of the Data

All values are expressed as mean±SEM. One-way analysis of variance was used to determine differences among groups for IS and AAR. Differences between groups in hemodynamics at various time points were compared by using a two-way analysis of variance (ANOVA) for time and treatment with repeated measures and Fisher's least significant difference (LSD) test if significant F ratios were obtained. Statistical differences were considered significant if the p value was <0.05.

Results

Hemodynamics:

Tables 1 and 2 summarize the mean±SEM for the hemodynamic parameters of heart rate (HR), mean arterial blood pressure (MBP), and rate-pressure product (RPP) analyzed at baseline, 30 minutes of occlusion and 2 hours of reperfusion. In Table 1, HR, MBP, and RPP at baseline were not significantly different among the groups. However, at 30 minutes of occlusion, the MBP in the lowBNTX+PC group was significantly higher compared to control, but by 2 hours of reperfusion, no differences in MBP were found between groups. In addition, RPP at 30 minutes of occlusion was significantly higher in the ischemic PC, BNTX, lowBNTX+PC, and hiBNTX+PC groups; however, the RPP at 2 hours of reperfusion was not significantly different in any of these groups. The HR in the NTB group was significantly lower at 2 hours of reperfusion, but there was no significant difference in MBP or RPP.

Table 2 shows that the HR in the ischemic PC group was significantly lower than control; however, HR in this group was not significantly different from control at 30 minutes of occlusion or 2 hours of reperfusion. The hiDAMGO group had a significantly lower HR compared to control at 2 hours of reperfusion. The medDAMGO and β-FNA+PC groups had a significantly lower MBP at 30 minutes of occlusion and 2 hours of reperfusion. In addition, MBP at 2 hours of reperfusion was significantly lower in the hiDAMGO and lownor-BNI+PC groups. RPP at 30 minutes of occlusion was significantly lower in the medDAMGO and b-FNA+PC groups. However, there were no significant differences in RPP among the groups at 2 hours of reperfusion.

Infarct Size and Area at Risk:

Left ventricular (LV) weight, area at risk (AAR), infarct size (IS), and IS as a percent of the AAR (IS/AAR) data are shown in Tables 3 and 4. In Table 3, the LV and AAR weights were not significantly different between groups. Infarct size was significantly smaller in the ischemic PC and both NTB+PC groups. The IS/AAR for the individual rat hearts are depicted in FIGS. 3 and 4 as well as the mean±SEM for each group (Table 3 and FIGS. 3 and 4). The control group had an average IS/AAR of 53.2±2.9%. Ischemic PC markedly reduced infarct size to 14.1±5.1% (*p<0.05 vs control). The low dose of the selective $\delta_1$-receptor antagonist, BNTX (1 mg/kg, iv), did not block ischemic PC (19.0±3.4%); whereas, the high dose of BNTX (3 mg/kg, iv) significantly attenuated the cardioprotective effect of ischemic PC (38.7±5.4%; *§p<0.05 vs control and ischemic PC; FIG. 3). Similarly, a dose response to NTB, a $\delta_2$-opioid receptor antagonist, was performed (FIG. 4). Neither dose (1 and 3 mg/kg, iv) of NTB inhibited the cardioprotective effect of ischemic PC (24.4±6.5 and 18.1±2.5%, respectively). BNTX or NTB alone had no effect on infarct size in nonpreconditioned groups (FIGS. 3 and 4).

Figure 6:
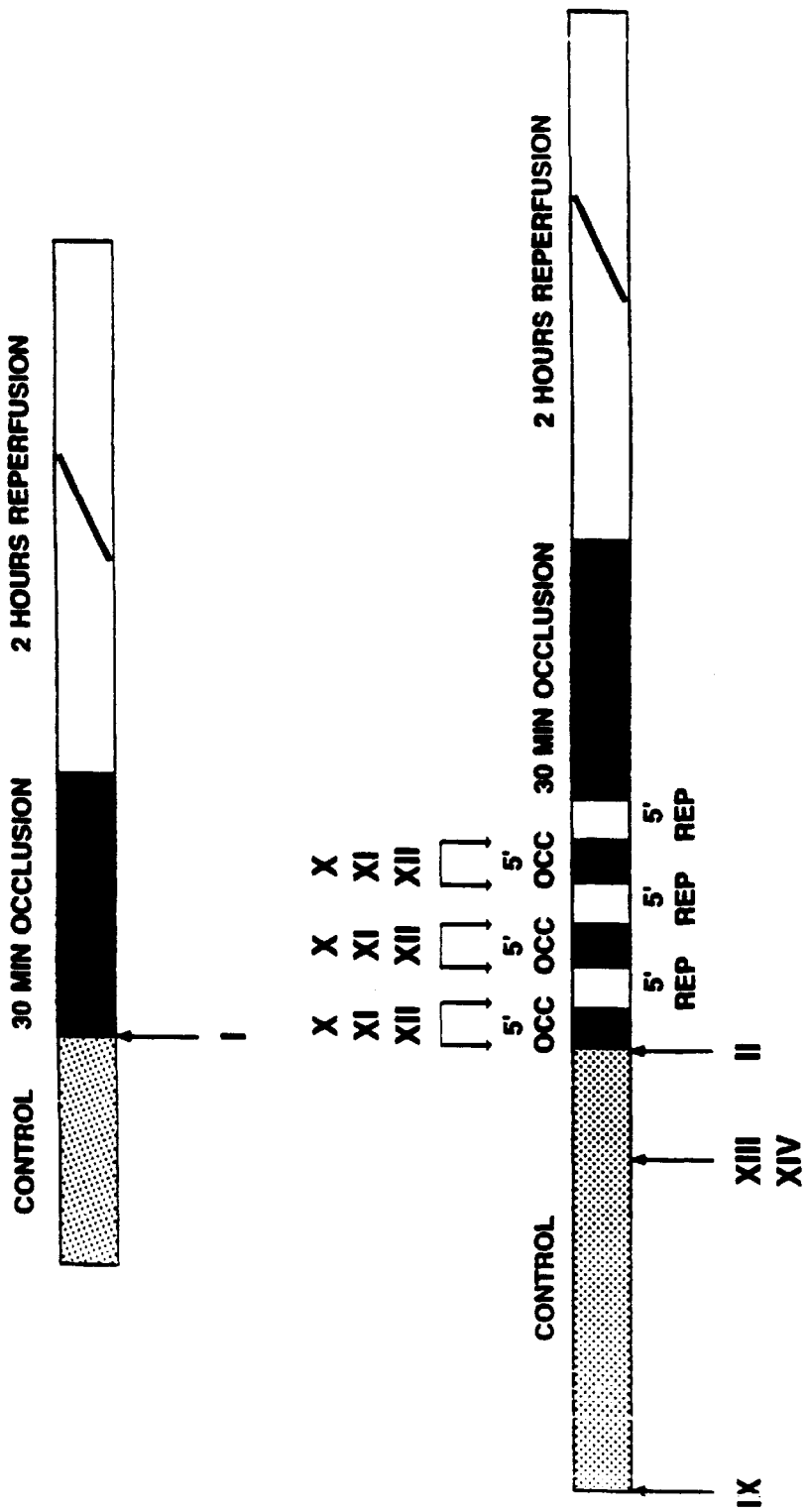
FIG. 6. Infarct sizes in rat hearts subjected to control (CON), 3×5 minute ischemic preconditioning (PC), nor-binaltrophimine (1 mg/kg, iv; norBNI), a $\kappa$-opioid receptor antagonist, given 15 minutes before ischemic PC (low norBNI+PC), and nor-binaltrophimine (5 mg/kg, iv) given 15 minutes before ischemic PC (hi norBNI+PC). Open circles indicate infarct sizes from individual hearts. Filled circles in each group indicate the average infarct size, mean±SEM with *p<0.05 vs control.

The results shown in Table 4 indicate that there were no significant differences in LV and AAR weights between the groups. Also, the results in Table 4 demonstrate that the IS and IS/AAR in ischemic PC, b-FNA+PC treated animals, and low- and hinor-BNI+PC groups were significantly lower compared to control. In addition, FIGS. 5 and 6 show the infarct sizes of the individual rat hearts and the mean±SEM for each group. The average IS in the control group was 54.7±3.7%. Ischemic PC significantly reduced IS/AAR (12.0±3.2%; *p<0.05 vs control). Twenty-four hour pretreatment (15 mg/kg, sc) with β-FNA, an irreversible μ-opioid receptor antagonist, did not abolish the cardioprotective effect of ischemic PC (8.0±1.7%; *p<0.05 vs control; FIG. 5). Furthermore, three doses (3×1, 10, and 100 mg/kg/5 minute infusion, iv) of DAMGO, a selective μ-opioid receptor agonist, did not mimic the cardioprotective effect of PC (53.9±4.3, 52.9±4.7, and 52.0±8.1%, respectively; FIG. 5). Finally, two doses (1 and 5 mg/kg, iv) of nor-BNI, a k-opioid receptor antagonist, given 15 minutes before ischemic PC did not block its protective effect (20.2±5.1 and 20.2±2.5%, respectively; FIG. 6).

Specificity of the Opioid Receptor Agonist and Antagonists:

Further studies were performed to demonstrate that the μ-opioid receptor agonist and antagonist were producing their effect via the μ-opioid receptor. It was observed that the three doses of DAMGO (3×1, 10, and 100 mg/kg/5 minute infusion equaling total doses of 3, 30, and 300 mg/kg, respectively) produced a dose-related reduction in blood pressure. Therefore, this decrease in blood pressure was the physiological parameter used to test the specificity of DAMGO and β-FNA toward the μ-opioid receptor and BNTX and NTB toward the delta (δ) opioid receptor. FIG.

7 shows the actions of the μ- and delta (δ) opioid receptor antagonists on the hypotension induced by DAMGO, the μ-opioid receptor agonist. Pretreatment for 24 hours with β-FNA (15 mg/kg, sc) abolished the vascular response to DAMGO; whereas, neither BNTX nor NTB blocked the hypotension induced by DAMGO. The decrease in blood pressure caused by the DPDPE dose response was antagonized by BNTX (data not shown). In addition, hypotensive responses to U-50488H were blocked by nor-BNI (data not shown). These data demonstrate that the opioid antagonists used appear to be specific for their respective receptors.

EXAMPLE 2

Role of $K_{ATP}$ channel and $G_{i/o}$ proteins in mediating ischemic PC.

This Example further illustrates the role of $K_{ATP}$ channels and $G_{i/o}$ proteins in meditating ischemic PC which results in the cardioprotective effect produced by delta-1 ($\delta_1$) opioid receptor activation.

The methodology described in Example 1, was essentially followed with regard to: general surgical procedures; preparation of drugs; determination of infarct size; and statistical analysis of the data.

Figure 8:
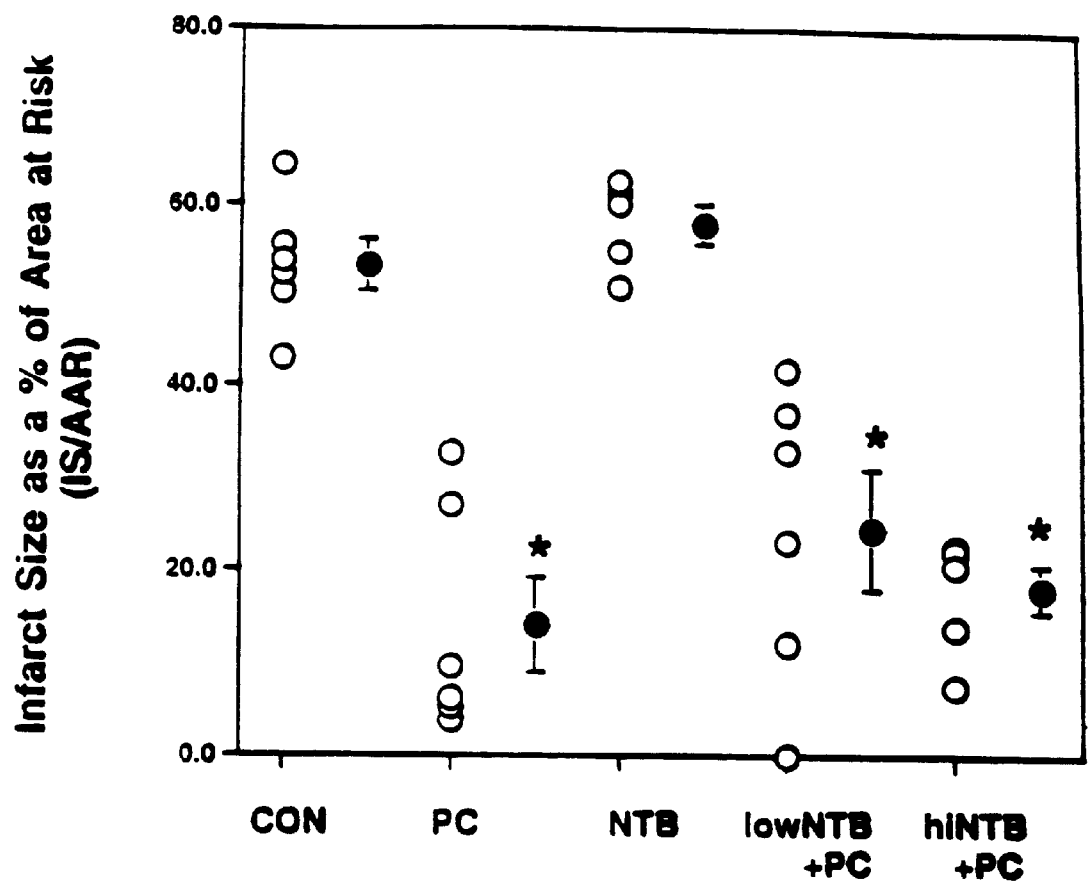
FIG. 8. Schematic chronological representation of the five experimental protocols followed in laboratory animals; comparing a control group (I) with groups (II, III, IV, and V) respectively treated with: (II) TAN67(−)(TAN)(delta-1 ($\delta_1$) opioid receptor agonist, produced by 15 minutes of TAN infusion (10 mg/kg, iv) prior to a 30 minute occlusion period); (III) BNTX (3 mg/kg, iv) (a delta-1 ($\delta_1$) opioid receptor antagonist, given 10 minutes before the 15 minute TAN infusion (BNTX+TAN)); (IV) glibenclamide (GLY, 0.3 mg/kg, iv) (a $K_{ATP}$ channel antagonist, given 45 minutes before the 15 minute TAN infusion (GLY+TAN)); and (V) pertussis toxin (PTX) (10 $\mu$g/kg, ip) (an inhibitor or $G_{i/o}$ proteins, administered 48 hours before the 15 minute TAN infusion (PTX+TAN)).

Study Groups and Experimental Protocols:

Animals were randomly assigned to one of five experimental studies. The control group was subjected to 30 minutes of occlusion and 2 hours of reperfusion (group I, n=6). Experiments were performed to test whether a $\delta_1$-opioid receptor agonist could mimic the protective effect of ischemic PC and which signal transduction pathway might be involved (FIG. 8). TAN 67(-) (10 mg/kg, iv), a nonpeptidic $\delta_1$-opioid receptor agonist, was infused for 15 minutes prior to the 30 minute occlusion period (group II, n=5). In group III, (n=6), BNTX (3 mg/kg, iv), a specific $\delta_1$-opioid receptor agonist, was given 10 minutes before the 15 minute TAN 67(-) infusion (10 mg/kg, iv) to test whether TAN67(-) is stimulating the $\delta_1$-opioid receptor. In group IV, (n=6), glibenclamide (0.3 mg/kg, iv), the $K_{ATP}$ channel antagonist, was given 30 minutes before the 15 minute infusion of TAN 67(-) to demonstrate an involvement of myocardial $K_{ATP}$ channels in $\delta_1$-opioid receptor-induced cardioprotection. Previously, we showed that glibenclamide when administered 30 minutes before, but not 5 minutes before the preconditioning stimuli completely abolished the cardioprotective effect (Schultz et al. *Am. J. Physiol.* 1997: 272:(*Heart Circ.Physiol.* 41):H2607–2615). Therefore, in this Example, we administered glibenclamide 30 minutes before TAN 67(-) infusion to allow time for antagonism of the $K_{ATP}$ channels. This dose of glibenclamide was shown previously in our laboratory to have no effect on infarct size in nonpreconditioned rats (Schultz et al. *Circ. Res.* 1996:78:1100–1104; Schultz et al. *Am. J. Physiol.* 1997: 272:(*Heart Circ.Physiol.* 41):H2607–2615). Group V (n=6) tested an interaction between $G_{i/o}$ proteins and the $\delta_1$-opioid receptor. Animals were pretreated with pertussis toxin (10 Tg/kg, ip), an inhibitor of $G_{i/o}$ proteins via ADP-ribosylation of the I-subunit, for 38 hours prior to the 15 minute TAN 67(-) infusion (10 mg/kg, iv). The dose of PTX was based on the protocol of Endoh et al. (Endoh et al. *Am. J. Physiol* 1985: 249:(*Heart Circ.Physiol.* 18):H309–H320) in which pertussis toxin (0.125–1.0 g/100 g Wistar rat body weight) dose-dependently attenuated the inhibitory effects of atrial muscarinic receptor activity. To demonstrate that pertussis toxin inhibited the G proteins, the changes in heart rate induced by acetylcholine and adenosine (responses previously shown to be mediated by $G_i$ proteins (Fleming et al. *Circulation* 1992:85:420–433) were measured. In a separate experiment consisting of four rats, acetylcholine (ACh, 0.15 mg/kg, iv) and adenosine (ADO, 1 mg/kg, iv) produced marked decreases in heart rate from 515±35 to 310±10 and 475±35 to 285±15 beats/min, respectively. These responses to ACh and ADO were completely abolished in six PTX-treated rats (PTX control heart rate of 450±10 vs PTX+ACh heart rate of 432±9 and PTX+ADO heart rate of 426±13). This dose of PTX had no effect on infarct size in nonpreconditioned rats (53.3±9.3% vs control IS/AAR of 55.6±2.1%).

Determination of Infarct Size:

After each experiment, the left coronary artery was reoccluded and Patent blue dye was injected into the venous catheter to stain the normally perfused region of the heart. The rat was euthanized with 15% KCl through the arterial catheter. The heart was excised and the left ventricle removed and sliced into five cross-sectional pieces. This procedure allowed for visualization of the normal, nonischemic region and the area of risk (AAR). The AAR was separated from the normal area using a dissecting scope (Cambridge Instruments). Both tissue regions (nonischemic and AAR) were incubated at 37° for 15 minutes in a 1% 2,3,5-triphenyltetrazolium stain in 100 mmol/L phosphate buffer (pH 7.4). TTC was used as an indicator to separate out viable and nonviable tissue (Klein et al. *Virchows Archives* 1981:393:287–297). The tissue was stored overnight in a 10% formaldehyde solution. The following day, the infarcted tissue was separated from the AAR by using the dissecting scope. The different regions (nonischemic, AAR, and infarct) were determined by gravimetry and infarct size (IS) was calculated as a % of the AAR (IS/AAR).

Exclusion Criteria:

A total of 32 animals were enrolled in the study. One animal in the control group was excluded due to intractable ventricular fibrillation. Two animals in the GLY+TAN group were excluded due to hypotension. A total of 29 animals completed the study.

Hemodynamics:

The mean±SEM data for heart rate (HR), mean arterial blood pressure (MBP), and rate-pressure product (RPP; heart rate×systolic blood pressure) measured before drug administration (baseline), 30 minutes of occlusion and 2 hours of reperfusion are summarized in Table 5. With the exception of the TAN group at baseline, there were no significant differences in HR between groups at any time point measured. MBP was significantly lower at baseline, 30 minutes of occlusion and 2 hours of reperfusion for the PTX+TAN group. In addition, TAN and the BNTX+TAN groups had a significantly lower MBP at 2 hours of reperfusion. The RPP was not significantly different among groups for any time point reported.

Blood glucose (mg/dL) levels were measured in the animals treated with glibenclamide prior to TAN 67(-) infuision (baseline=169±21; 15 minute occlusion=133±23; 15 reperfusion=95±4*; 1 hour reperfusion=76±5*; 2 hours reperfusion=77±7*, *p<0.05 vs baseline). Blood glucose significantly decreased approximately 1–1.5 hours after its administration similar to that seen previously in this laboratory (Schultz et al. *J. Mol. Cell Cardiol.* 1997:29:2187–2195).

TABLE 5

Hemodynamic Data

| | | BASELINE | | | 30 MIN OCC | | | 2 HOURS REP | | |
|---|---|---|---|---|---|---|---|---|---|---|
| | n | HR | MBP | RPP | HR | MBP | RPP | HR | MBP | RPP |
| Control | 6 | 393 ± 12 | 84 ± 10 | 38 ± 5 | 373 ± 14 | 68 ± 6 | 29 ± 3 | 44 ± 8 | 81 ± 10 | 37 ± 7 |
| TAN | 5 | 350 ± 13* | 73 ± 8 | 32 ± 2 | 342 ± 12 | 62 ± 5 | 28 ± 2 | 414 ± 13 | 54 ± 3* | 31 ± 1 |
| BNTX + TAN | 6 | 405 ± 15 | 88 ± 5 | 43 ± 3 | 340 ± 26 | 59 ± 8 | 27 ± 5 | 415 ± 30 | 50 ± 8* | 29 ± 2 |
| GLY + TAN | 6 | 380 ± 10 | 86 ± 6 | 39 ± 3 | 362 ± 11 | 62 ± 5 | 30 ± 4 | 436 ± 19 | 61 ± 6 | 36 ± 2 |
| PTX + TAN | 6 | 378 ± 7 | 57 ± 4* | 34 ± 2 | 370 ± 9 | 51 ± 3* | 29 ± 1 | 458 ± 7 | 47 ± 7* | 33 ± 4 |

Abbreviations:
HR, heart rate (beats/min). MBP, mean arterial blood pressure (mmHg). RPP, rate-pressure product (mmHg/min/1000). TAN, 15 minute infusion of TAN67(−) (10 mg/kg, iv); Λ1-opioid receptor agonist, followed by 30 minutes of occlusion and 2 hours of reperfusion. BNTX + TAN, BNTX (3 mg/kg, iv), Λ1-opioid receptor antagonist, given 10 minutes before the 15 minute TAN67(−) infusion. PTX + TAN, 48 hour pretreatment with pertussis toxin (10 μg/kg, ip), an inhibitor of Gi/o proteins, prior to TAN67(−) infusion.
Values given as mean ± S.E.M. Among group, *p < 0.05 vs. control.

Figure 9:
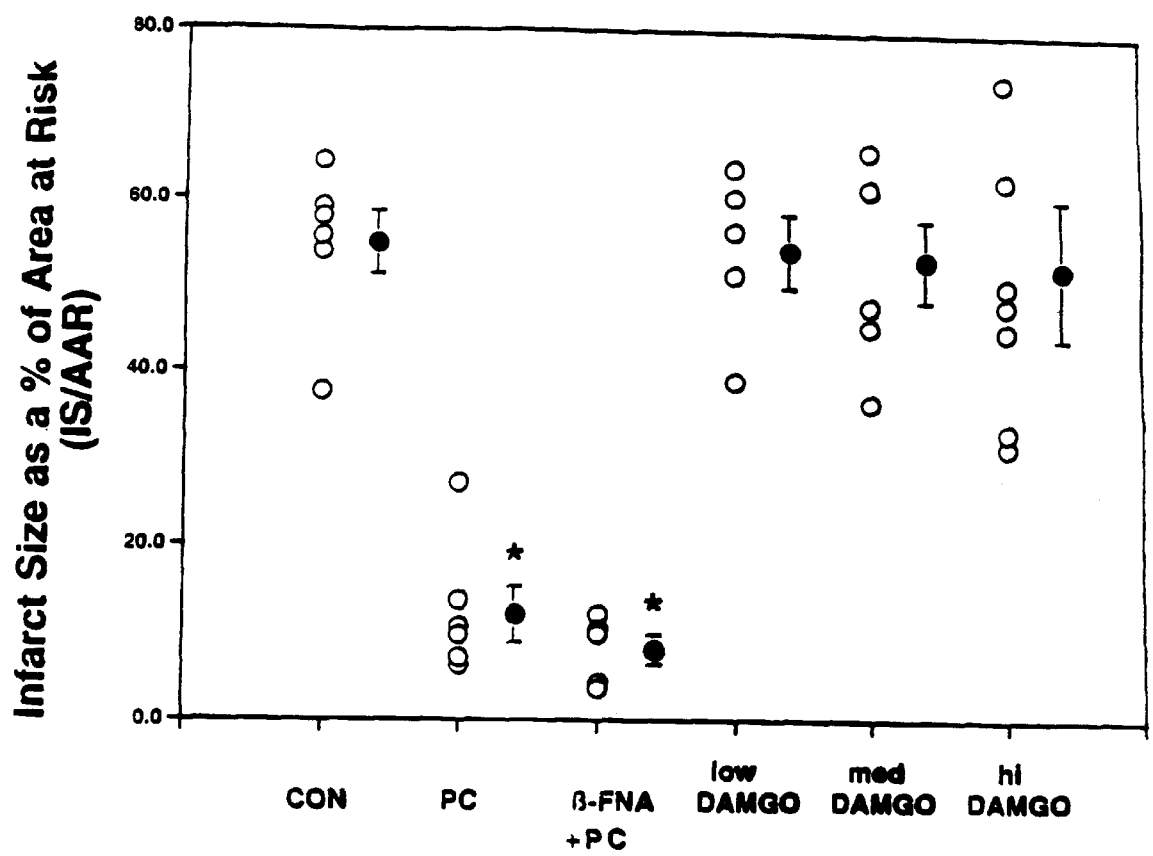
FIG. 9. Graphical representation showing the IS/AAR for the individual rat hearts and the mean±SEM for each group. The average IS/AAR for the control group was 55.6±2.1%. Data are presented for laboratory animal groups treated: with TAN67(−); BNTX followed by treatment with TAN67 (−); glibenclamide followed by treatment with TAN67(−); and pertussis toxin (PTX) followed by treatment with TAN67(−).

Infarct Size and Area at Risk:

Table 6 depicts the weights in grams of the left ventricle (LV), area at risk (AAR), and infarct size (IS). In addition, infarct size data expressed as a percent of the area at risk (IS/AAR), a measure of cardioprotection, are shown in Table 6 and FIG. 2. The LV weight in the BNTX+TAN group was significantly smaller compared to control; however, there were no significant differences among groups in AAR weights. TAN 67(−)-treated groups had a significantly lower infarct size compared to control. FIG. 9 shows IS/AAR for the individual rat hearts and the mean+SEM for each group. The average IS/AAR for the control group was 55.6±2.1%. A 15 minute infusion period of TAN 67(−) (10 mg/kg, iv), the nonpeptidic $\delta_1$-opioid receptor agonist, significantly reduced infarct size as compared to the control group (27.1±4.8%, *p<0.05). The cardioprotection induced by TAN 67(−) was completely abolished by BNTX (3 mg/kg, iv), a selective $\delta_1$-opioid receptor agonist, indicating that TAN produces its cardioprotective effect via $\delta_1$-opioid receptors. Furthermore, $\delta_1$-opioid receptor-induced cardioprotection appears to be mediated via the $K_{ATP}$ channel since glibenclamide (0.3 mg/kg, iv) administered 45 minutes before the TAN 67(−) infusion completely blocked the cardioprotection (53.0±5.4%; GLY+TAN). A role for $G_{i/o}$ proteins was also shown to be involved in the cardioprotective effect of TAN 67(−) since a 48 hour pretreatment with pertussis toxin (10 μg/kg, ip), an inhibitor of $Gi_{1o}$ proteins, abolished the cardioprotective effect induced by TAN 67(−) (60.8±3.6%; PTX+TAN).

TABLE 6

Infarct Size Data

| | n | LV | AAR | IS | IS/AAR |
|---|---|---|---|---|---|
| Control | 6 | 0.857 ± 0.064 | 0.423 ± 0.055 | 0.234 ± 0.030 | 55.6 ± 2.1 |
| TAN | 5 | 0.739 ± 0.035 | 0.404 ± 0.039 | 0.116 ± 0.031* | 27.1 ± 4.8* |
| BNTX + TAN | 6 | 0.680 ± 0.070* | 0.333 ± 0.043 | 0.174 ± 0.028 | 51.3 ± 3.3 |
| GLY + TAN | 6 | 0.718 ± 0.038 | 0.364 ± 0.045 | 0.189 ± 0.021 | 53.0 ± 5.4 |
| PTX + TAN | 6 | 0.828 ± 0.027 | 0.437 ± 0.053 | 0.273 ± 0.047 | 60.8 ± 3.6 |

Abbreviations:
n, number of animals. LV, left ventricle in grams. AAR, area at risk in grams. IS, infarct size in grams. IS/AAR, infarct size as a % AAR. TAN, 15 minute infusion of TAN67(−) (10 mg/kg, iv), δ1-opioid receptor agonist, followed by 30 minutes of occlusion and 2 hours of reperfusion. BNTX + TAN, BNTX (3 mg/kg, iv), δ1-opioid receptor antagonist, given 10 minutes before the 15 minute TAN67(−) infusion. GLY + TAN, glibenclamide (0.3 mg/kg, iv), KATP channel antagonist; given 30 minutes before the 15 minute TAN67(−) infusion. PTX + TAN, 48 hour pretreatment with pertussis toxin (10 μg/kg, ip), an inhibitor of Gi/o proteins, before TAN67(−)infusion.
Values given as mean ± S.E.M. There are no significant differences among the groups for the AAR sizes. IS and IS/AAR in TAN hearts showed a significant difference compared to control (*p < 0.05 vs. control).

Discussion

The present results indicate that the nonpeptidic $\delta_1$-opioid receptor agonist, TAN 67(−), reduced infarct size and elicited a cardioprotective effect via $\delta_1$-opioid receptor stimulation (27.1±4.8%, *p<0.05 vs control; FIG. 9). These findings support our current hypothesis and previous findings that $\delta_1$-opioid receptors are involved in the cardioprotective effect of ischemic PC. Previously, TAN 67(−) has been shown to be selective for the $\delta_1$-opioid receptor having a high affinity for $\delta_1$-opioid receptors with a 2070-fold lower affinity at the μ-opioid receptor and 1600-fold lower affinity at the κ-opioid receptor. In addition, the cardioprotective effect afforded by TAN 67(−) infusion was completely abolished by BNTX, a selective $\delta_1$-opioid receptor antagonist, which demonstrates that TAN 67(−) is most likely stimulating the $\delta_1$-opioid receptor to elicit cardioprotection. The involvement of a $\delta_1$-opioid receptor mechanism in cardioprotection of the rat heart supports and extends the results of Mayfield and D'Alecy (Mayfield, K. P., et al., *J Pharmacol Exp Ther* (1994) 268:683–688 and *J Pharmacol Exp Ther* (1994) 268:74–77). This group demonstrated that the synthetic $\delta_1$-opioid receptor agonist, DPDPE, increased the survival time of mice subjected to hypoxia and this protection was abolished by BNTX. Similarly, Chien and colleagues (Chien et at. *J. Thorac. Cardiovasc. Surg.* 1994:107:964–967) also demonstrated that $\delta_1$-opioid receptor stimulation with the synthetic δ-agonist, DADLE, increased tissue preservation time up to 48 hours for several canine organ systems (heart, lung, liver, kidney) prior to transplantation.

To further clarify the cellular mechanisms by which activation of the $\delta_1$-opioid receptor produces cardioprotection in the rat, we studied the role of $G_{i/o}$ proteins and the $K_{ATP}$ channel in mediating this effect. The $\delta_1$-opioid receptor has been well documented to be linked to $K^+$ channels via G proteins in neuronal tissue (Ikeda et al. *Biochem. Biophys. Res. Comm.* 1995:208:302–308; North et al. *Proc. Natl. Acad. Sci. USA* 1987:84:5487–5491; Wild et al. *Eur. J. Pharmacol.* 1991:193:135–136; Williams et al. *Nature* 1982:299:74–77). Wild et al. (*Eur. J. Pharmacol.* 1991:193:135–136) demonstrated that the antinociceptive effect produced by $\delta_1$-opioid receptor activation was mediated via $K^+$ channels and the subtypes of this receptor were linked to different $K^+$channels. Their results demonstrated that the analgesia produced by the $\delta_1$-opioid receptor agonist, DPDPE, could be antagonized by glibenclamide, indicating that the $\delta_1$-receptor subtype was linked to neuronal $K_{ATP}$ channels (Wild et al. *Eur. J. Pharmacol.* 1991:193:135–136). However, the antinociceptive effect of deltorphin II, a $\delta_2$-opioid receptor agonist, was not blocked by glibenclamide but was antagonized by tetraethylammonium bromide (TEA), a voltage-gated $K^+$ channel blocker, which demonstrates that the $\delta_2$-receptor subtype was linked to $K^+$ channels other than the $K_{ATP}$ channel (Wild et al. *Eur. J. Pharmacol.* 1991:193:135–136). Our present results show that the cardioprotection induced by TAN 67(-), a $\delta_1$-agonist, was blocked by glibenclamide which indicates that the myocardial protection is mediated by an interaction between the $\delta_1$-opioid receptor and the myocardial $K_{ATP}$ channel (FIGS. 8 and 9). These data agree with our previous results which showed that morphine-induced cardioprotection was mediated through a $K_{ATP}$ channel-linked mechanism (Schultz, J. J. et al., *Circ Res* (1996) 78:1100–1104). Recently, Ytrehus and colleagues (Ytrehus et al. *J. Mol. Cell Cardiol.* 1997:29:A14) indicated that in the isolated buffer-perfused rat heart, there is an association between opioid receptors, lipoxygenase, protein kinase C and $K_{ATP}$ channels in mediating ischemic PC against myocardial infarction.

$G_{i/o}$ protein-coupled muscarinic and adenosine receptors have been shown to induce the cardioprotective effect of ischemic PC (Lasley et al. *J. Mol. Cell Cardiol.* 1993:25:815–821; Liu et al. *Circulation* 1991:84:350–356; Qian et al. *Am. J. Physiol.* 1996: 271:(*Heart Circ. Physiol.* 40):H23–H28; Yao et al. *Am. J. Physiol.* 1993: 264:(*Heart Circ.Physiol.* 34):H2221–H2225; Yao et al. *Circ. Res.* 1993:73:1193–1201). There has been speculation that cardioprotection produced by these G protein coupled receptors is mediated by the interaction of the I subunit from the $G_i$ protein and the myocardial $K_{ATP}$ channel (Ito et al. *J. Gen. Physiol.* 1992:99:961–983; Kirsch et al. *Am. J. Physiol.* 1990: 259:(*Heart Circ. Physiol.* 28):H820–H826; Kurachi et al. *Trends Cardiovasc. Med.* 1994:4:64–69; Kurachi et al. *Progress Neurobiol.* 1992:39:229–246). Opioid receptors belong to this family of G protein coupled receptors. Opioid receptors (T, Λ, and P) have been demonstrated to be linked to $K^+$channels via $G_i$ proteins (Chen et al. *J. biol Chem.* 1994:269:7839–7842; Childers *Life Sci.* 1991:48:1991–2003; Cox et al. In: Herz A., ed. *Handbook of Experimental Pharmacology: Opioids I*. New York: Springer-Verlag; 1993: 143–188; Ikeda et al. *Biochem. Biophys. Res. Comm.* 1995:208:302–308; North et al. *Proc. Natl. Acad. Sci. USA* 1987:84:5487–5491). Our present results clearly indicate that pertussis toxin abolished the cardioprotection induced by the $\delta_1$-opioid receptor agonist, TAN 67(-) (FIG. 9) which suggests a role of $G_{i/o}$ proteins in $\delta_1$-opioid receptor mediated myocardial protection. A number of physiological responses of $\delta_1$-opioid receptor stimulation including inhibition of adenylate cyclase activity, cell proliferation, and inhibition of cardiac β-adrenergic effects have also been shown to be pertussis toxin-sensitive (Ela et al. *J. Mol. Cell Cardiol.* 1997:29–711–720; Law et al. *Mol. Pharmacol.* 1997:51:152–160; McKenzie et al. *Biochem. J.* 1990:267:391–398; Pepe et al. *Circulation* 1997:95:2122–2129; Xiao et al. *Am. J. Physiol.* 1997: 272: (*Heart Circ. Physiol.* 41):H797–H805).

Figure 10:
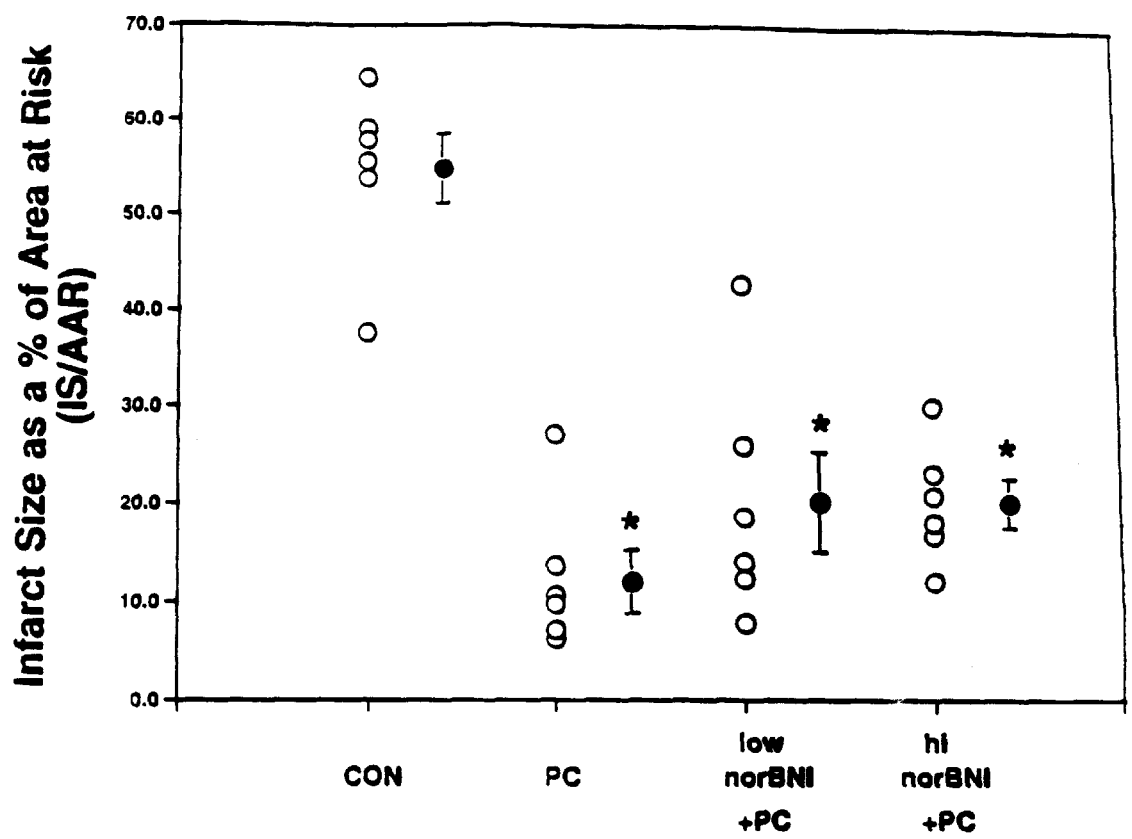
FIG. 10. Schematic depiction of the rat myocardial membrane depicting cardioprotection produced by activation of opioid receptors. The delta-1 ($\delta_1$) opioid receptors in a cell membrane activated by binding to an opioid, with concomitant interaction of the delta-1 ($\delta_1$) opioid receptor with the myocardial stimulating the opening of $K_{ATP}$ channels interacting with $G_{i/o}$ proteins.
Figure 11:
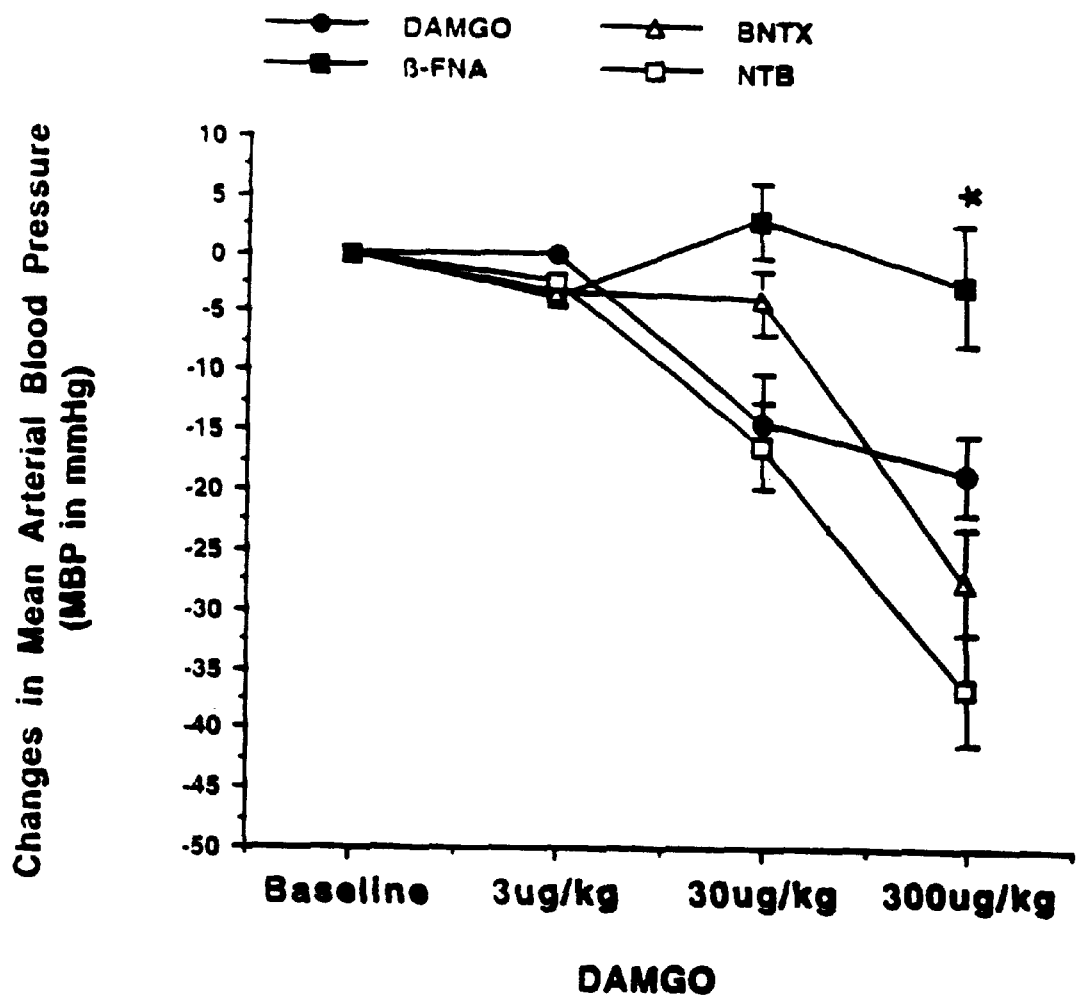
FIGS. 11–14 show further results of the invention relating to blood pressure, reperfusion, infarct size and potassium transport.
Figure 12:
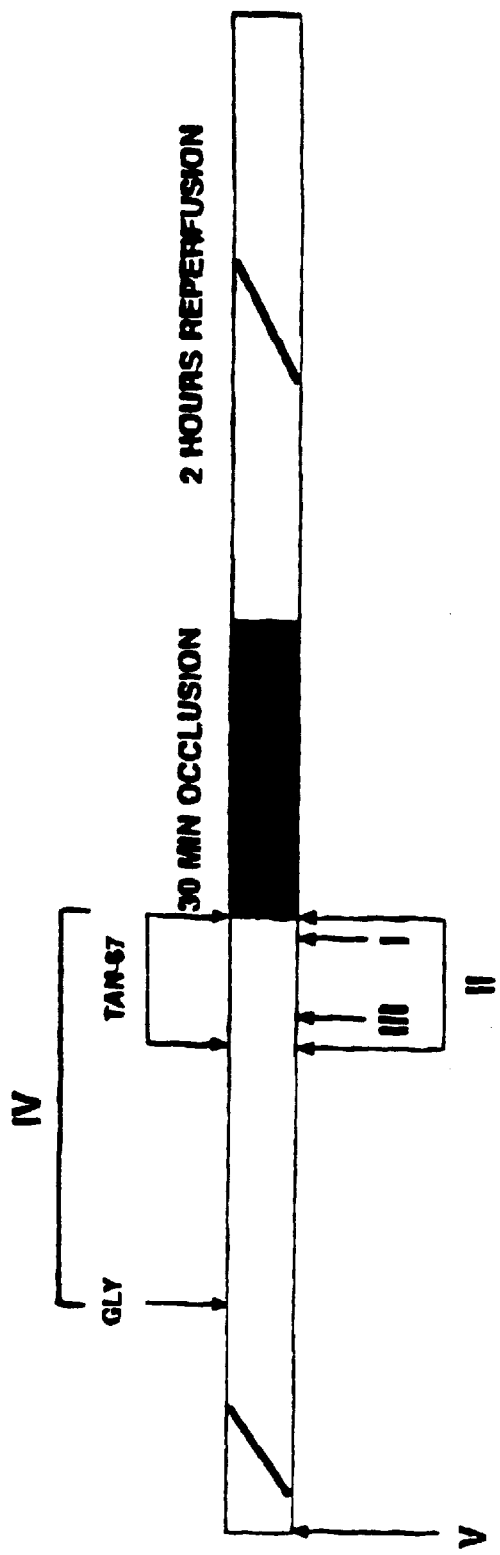
Figure 13:
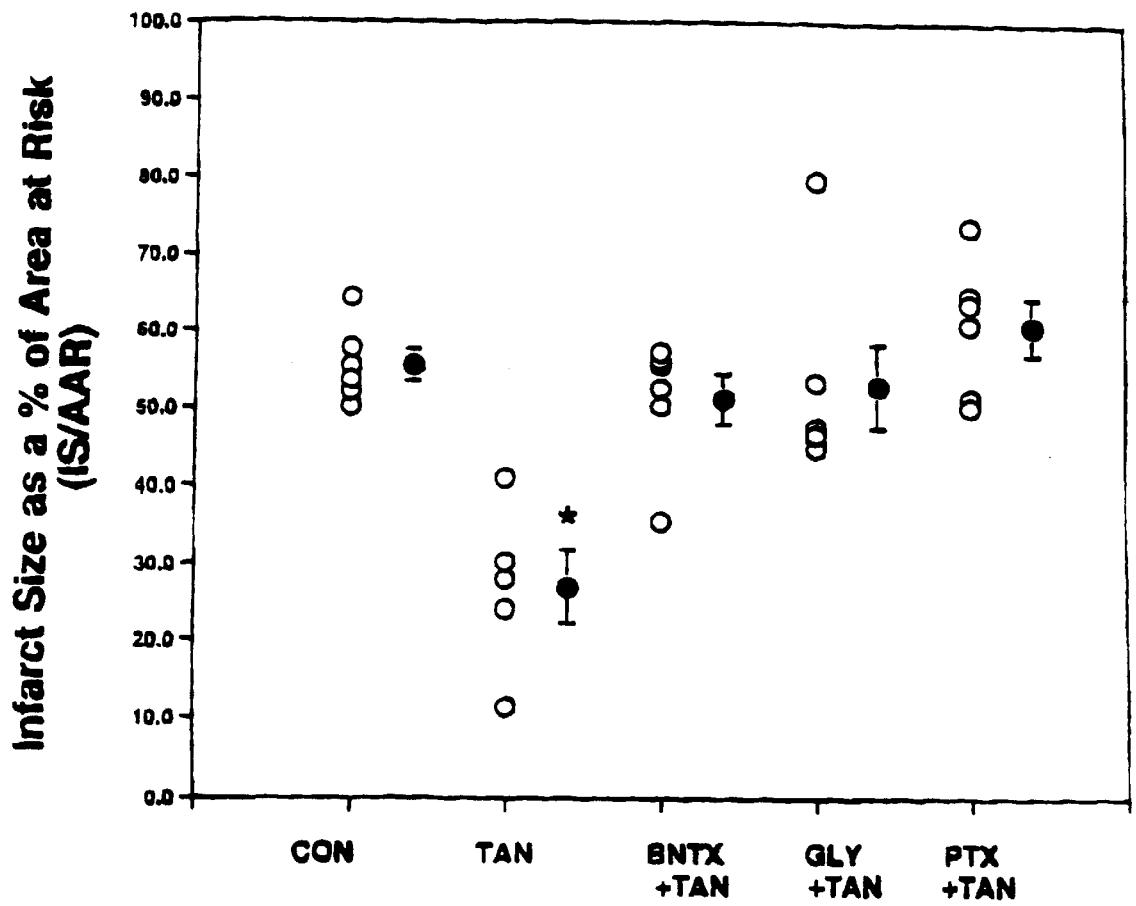
Figure 14:
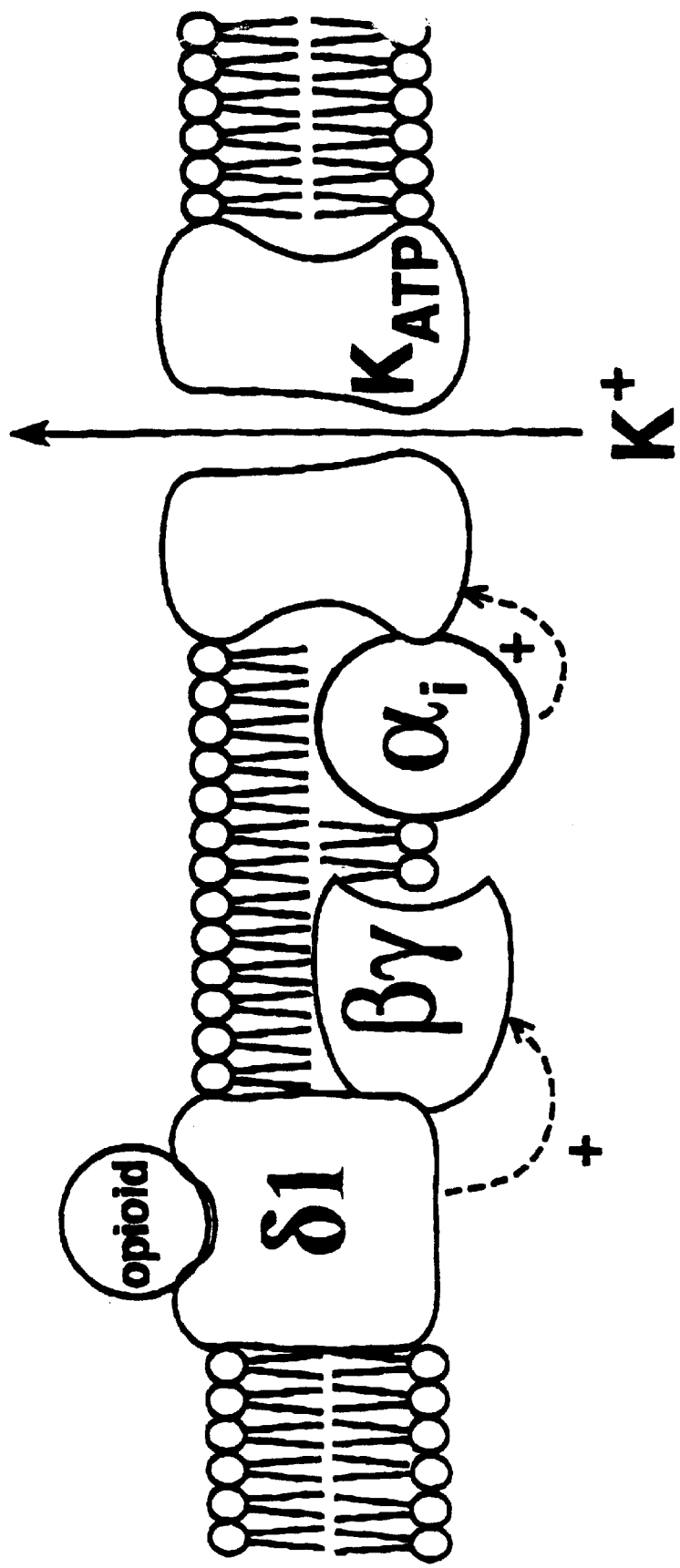

In summary, TAN 67(-), a $\delta_1$-opioid receptor agonist, produced a reduction in infarct size in the rat. The results of this study are the first to demonstrate that the mechanism of $\delta_1$-opioid receptor-mediated cardioprotection involves an interaction with the myocardial $K_{ATP}$ channel and $G_{i/o}$ proteins in the rat heart (FIG. 10). Although not the focus of the present study, second messengers such as protein kinase C (PKC), protein kinase A (PKA), and tyrosine kinase may have a role in the cardioprotective effect induced by $\delta_1$-opioid receptor stimulation. Both PKC and tyrosine kinase have been implicated in ischemic preconditioning (Imagawa et al. *J. Mol. Cell Cardiol.* 1997:29:1885–1893; Li et al. *Am. J. Physiol.* 1995:268:(*Heart Circ. Physiol.* 37):H426–431; Maulik et al. *FEBS Letters* 1996:396:233–237; Speechly-Dick et al. *Circ. Res.* 1994:75:586–590; Ytrehus et al. *Am. J. Physiol.* 1994: 266:(*Heart Circ. Physiol.):H*1145–H1152; Ytrehus et al. *J. Mol. Cell Cardiol.* 1997:29:A14) and along with PKA to interact with δ-opioid receptors in cardiac and neuronal tissue (Chen et al. *J. biol. Chem.* 1994:269:7839–7842; Childers *Life Sci.* 1991:48:1991–2003; Ela et al. *J. Mol. Cell Cardiol.* 1993:26:599–613; Law etal. *Mol. Pharmacol.* 1997:51:152–160; Lou et al. *Biochem. Biophys. Res. Comm.* 1997:236:626–629; Ytrehus et al. *J. Mol. Cell Cardiol.* 1997:29:A14). However, North and colleagues (North et al. *Proc. Natl. Acad. Sci. USA* 1987:84:5487–5491) concluded that cAMP-dependent protein kinase and PKC are not directly involved in the coupling between the δ-opioid receptor and $K^+$ channel in the guinea pig submucous plexus. Childers (Childers *Life Sci.* 1991:48:1991–2003) also stated that the effects of δ-agonists in opening potassium channels are not mediated via second messengers but instead through direct interaction between G-proteins and ion channels. Therefore, further studies need to be performed to determine the involvement of various kinases in $\delta_1$-opioid receptor mediate cardioprotection. These results have provided evidence for a physiological role of $\delta_1$-opioid receptors in the cardiovascular system and have enhanced our understanding of the mechanism(s) by which this receptor elicits a cardioprotective effect. These findings have important clinical ramifications since synthetic opioid derivatives will not only alleviate pain postoperatively but may also provide a cardioprotective effect to patients receiving cardiac surgical interventions if these agents are administered preoperatively.

Each of these publications is hereby incorporated herein by reference. Said publications relate to the art to which this invention pertains. The references cited above are each incorporated by reference herein, whether specifically incorporated or not.

We claim:

1. A method for reducing ischemic damage to an organ having a delta δ opioid receptor in a mammal, comprising the step of:
administering to said mammal a therapeutically effective amount of an agonist to the delta δ opioid receptor in a suitable carrier,
wherein the agonist is represented by the formula:

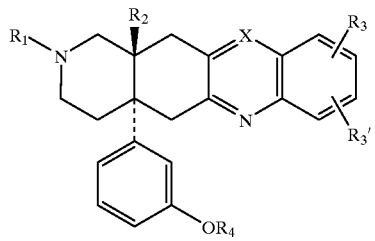

wherein $R_1$ represents a hydrogen atom, an alkyl group having 1–5 carbon atoms, a cycloalkylalkyl group having 4–7 carbon atoms, a cycloalkenylalkyl group having 5–7 carbon atoms, an aralkyl group having 7–14 carbon atoms, an alkenyl group having 4–5 carbon atoms, an allyl group, a furan-2-yl alkyl group, a thiophen-2-yl alkyl group, an alkanoyl group having 1–5 carbon atoms, a benzoyl group, a vinyloxycarbonyl group, a 2,2,2-trichloroethoxycarbonyl group, a benzyloxycarbonyl group, or an arylalkanoyl group having 8–14 carbon atoms;
$R_2$ represents a hydrogen atom or $OR_5$, wherein $R_5$ represents a hydrogen atom or an alkanoyl group having 1–5 carbon atoms;
$R_3$ and $R_3'$ each independently represents a hydrogen atom, an alkyl group having 1–5 carbon atoms, fluorine, chlorine, bromine, iodine, an alkoxy group having 1–5 carbon atoms, a nitro group, an amino group, or an alkylamino group;
$R_4$ represents a hydrogen atom, an alkyl group having 1–3 carbon atoms, a benzyl group, or an alkanoyl group having 1–5 carbon atoms; and
X represents CH or N.

2. The method as in claim 1, wherein the mammal is a human.

3. The method as in claim 1, wherein the organ is the heart.

4. The method as in claim 1, wherein in the formula $R_1$ is an alkyl group having 1–5 carbon atoms, a cycloalkylalkyl group having 4–7 carbon atoms, an aralkyl group having 7–14 carbon atoms, an alkenyl group having 4–5 carbon atoms, or an allyl group.

5. The method as in claim 1, wherein the agonist is administered in a cardioplegic solution.

6. A method for reducing ischemic damage to an organ having a delta δ opioid receptor in a mammal, comprising the step of:
administering to said mammal a therapeutically effective amount of an agonist to the delta δ opioid receptor in a suitable carrier, wherein the opioid receptor agonist is selected from the group consisting of DPDPE, BW373U86, DADLE, SB219825, SNC80 and SIOM.

7. A method for inducing cardioprotective effect in a mammal, comprising:
administering a therapeutically effective amount of a delta δ opioid receptor agonist in a suitable carrier, wherein the agonist is represented by the formula:

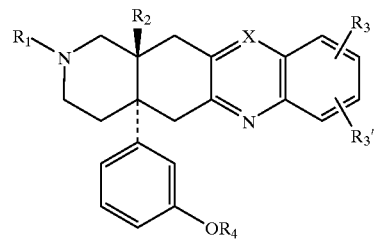

wherein $R_1$ represents a hydrogen atom, an alkyl group having 1–5 carbon atoms, a cycloalkylalkyl group having 4–7 carbon atoms, a cycloalkenylalkyl group having 5–7 carbon atoms, an aralkyl group having 7–14 carbon atoms, an alkenyl group having 4–5 carbon atoms, an allyl group, a furan-2-yl alkyl group, a thiophen-2-yl alkyl group, an alkanoyl group having 1–5 carbon atoms, a benzoyl group, a vinyloxycarbonyl group, a 2,2,2-trichloroethoxycarbonyl group, a benzyloxycarbonyl group, or an arylalkanoyl group having 8–14 carbon atoms;
$R_2$ represents a hydrogen atom or $OR_5$, wherein $R_5$ represents a hydrogen atom or an alkanoyl group having 1–5 carbon atoms;
$R_3$ and $R_3'$ each independently represents a hydrogen atom, an alkyl group having 1–5 carbon atoms, fluorine, chlorine, bromine, iodine, an alkoxy group having 1–5 carbon atoms, a nitro group, an amino group, or an alkylamino group;
$R_4$ represents a hydrogen atom, an alkyl group having 1–3 carbon atoms, a benzyl group, or an alkanoyl group having 1–5 carbon atoms; and
X represents CH or N.

8. The method of claim 7, wherein in the formula $R_1$ is an alkyl group having 1–5 carbon atoms, a cycloalkylalkyl group having 4–7 carbon atoms, an aralkyl group having 7–14 carbon atoms, an alkenyl group having 4–5 carbon atoms, or an allyl group.

9. The method of claim 7, wherein the mammal is a human.

10. The method as in claim 7, wherein the agonist is administered in a cardioplegic solution.

11. A method for inducing a cardioprotective effect in a mammal, comprising:
administering a therapeutically effective amount of a delta δ opioid receptor agonist in a suitable carrier, wherein the opioid receptor agonist is selected from the group consisting of: DPDPE, BW373U86, DADLE, SB219825, SNC80 and SIOM.

* * * * *